US012617827B2

(12) United States Patent
Muraoka et al.

(10) Patent No.: US 12,617,827 B2
(45) Date of Patent: May 5, 2026

(54) SELF-ASSEMBLING PEPTIDE

(71) Applicants: NATIONAL UNIVERSITY CORPORATION TOKYO MEDICAL AND DENTAL UNIVERSITY, Tokyo (JP); KANAGAWA INSTITUTE OF INDUSTRIAL SCIENCE AND TECHNOLOGY, Ebina (JP)

(72) Inventors: Takahiro Muraoka, Tokyo (JP); Atsuya Yaguchi, Tokyo (JP); Itsuki Ajioka, Tokyo (JP); Go Watanabe, Sagamihara (JP)

(73) Assignees: NATIONAL UNIVERSITY CORPORATION TOKYO MEDICAL AND DENTAL UNIVERSITY, Tokyo (JP); KANAGAWA INSTITUTE OF INDUSTRIAL SCIENCE AND TECHNOLOGY, Ebina (JP)

( * ) Notice: Subject to any disclaimer, the term of this patent is extended or adjusted under 35 U.S.C. 154(b) by 818 days.

(21) Appl. No.: 17/999,313

(22) PCT Filed: Jul. 29, 2021

(86) PCT No.: PCT/JP2021/028175
§ 371 (c)(1),
(2) Date: Nov. 18, 2022

(87) PCT Pub. No.: WO2022/025209
PCT Pub. Date: Feb. 3, 2022

(65) Prior Publication Data
US 2023/0203116 A1 Jun. 29, 2023

(30) Foreign Application Priority Data
Jul. 30, 2020 (JP) ................................. 2020-128805
Sep. 1, 2020 (JP) ................................. 2020-146597

(51) Int. Cl.
| | |
|---|---|
| *C07K 14/475* | (2006.01) |
| *A61K 9/06* | (2006.01) |
| *A61K 38/00* | (2006.01) |
| *A61K 47/42* | (2017.01) |
| *A61P 9/00* | (2006.01) |
| *A61P 25/28* | (2006.01) |
| *C07K 14/00* | (2006.01) |
| *C07K 14/50* | (2006.01) |
| *C07K 14/78* | (2006.01) |

(52) U.S. Cl.
CPC ............. *C07K 14/475* (2013.01); *A61K 9/06* (2013.01); *A61K 47/42* (2013.01); *A61P 9/00* (2018.01); *A61P 25/28* (2018.01); *C07K 14/001* (2013.01); *C07K 14/4753* (2013.01);
*C07K 14/50* (2013.01); *C07K 14/78* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 2009/0162437 A1 | 6/2009 | Horii et al. | |
| 2015/0005228 A1 | 1/2015 | Yang et al. | |

FOREIGN PATENT DOCUMENTS

| | | | |
|---|---|---|---|
| CN | 108997487 A | 12/2018 | |
| JP | 2010504972 A | 2/2010 | |
| JP | 2016528018 A | 9/2016 | |
| WO | 2014035345 A1 | 3/2014 | |
| WO | 2014133027 A1 | 9/2014 | |
| WO | 2015027203 A1 | 2/2015 | |
| WO | 2020171161 A1 | 8/2020 | |

OTHER PUBLICATIONS

Vahedifar and Wu, Trends in Food Science & Technology 119 (2022) 476-494 (Year: 2022).*
Campbell et al., "hypothetical protein A6R68_06599, partial [Neotoma lepida]", Database GenBank, 2016, Database accession No. OBS64850. 1, XP93146195, Abstract.
Hara et al., "ROS-Triggered Gel-Sol Transition and Kinetics-Controlled Cargo Release by Methionine-Containing Peptides", ChemBioChem, 2023, vol. 24, No. 9, e202200798 pp. 1-7.
Search Report for Corresponding European Application No. 21850578. 2, Apr. 17, 2024, 10 pages.
Vukicevic et al., "Identification of Multiple Active Growth Factors in Basement Membrane Matrigel Suggests Caution in Interpretation of Cellular Activity Related to Extracellular Matrix Components", Experimental Cell Research, 1992, vol. 202, pp. 1-8.
Vallier et al., "Activin/Nodal and FGF pathways cooperate to maintain pluripotency of human embryonic stem cells", Journal of Cell Science, 2005, vol. 118, vol. 19, pp. 4495-4509.
Cooperman et al., "The immunogenicity of injectable collagen. I. A 1-year prospective study", Journal of the American Academy of Dermatology, 1984, vol. 10, No. 4, pp. 638-646.

(Continued)

*Primary Examiner* — Christina M Borgeest
(74) *Attorney, Agent, or Firm* — Lucas & Mercanti, LLP

(57) ABSTRACT

An object is to provide a peptide gelling agent which gels under physiological conditions and which has a relatively short chain length, and a sustained-release gel based on the gelling agent. A hydrogelling self-assembling peptide is provided having one or two core peptides with an amino acid sequence of the formula: Xaa-Yaa-Zaa-Yaa-Xaa-Yaa-Zaa-Yaa-Xaa, wherein Xaa is independently Ile or Met, Yaa is independently Asp, Glu, Lys, or Arg, and Zaa is independently Ala or Gly. The full length of the amino acid sequence constituting the self-assembling peptide is 25 amino acids or less.

24 Claims, 15 Drawing Sheets

Specification includes a Sequence Listing.

(56)      References Cited

OTHER PUBLICATIONS

Lynn et al., "Antigenicity and Immunogenicity of Collagen", Journal of Biomedical Materials Research Part B Applied Biomaterials, 2004, vol. 71, pp. 343-354.

Scott et al., "Compelling transgenetic evidence for transmission of bovine spongiform encephalopathy prions to humans", PNAS, 1999, vol. 96, No. 26, pp. 15137-15142.

Dasgupta et al., "Peptide hydrogels", RSC Advances, 2013, vol. 3, pp. 9117-9149.

Jonker et al., "Peptide- and Protein-Based Hydrogels", Chemistry of Materials, 2012, vol. 24, pp. 759-773.

Zhang et al., "Spontaneous assembly of a self-complementary oligopeptide to form a stable macroscopic membrane", Proc. Natl. Acad. Sci. USA, 1993, vol. 90, pp. 3334-3338.

Zhang et al., "Unusually Stable B-Sheet Formation in an Ionic Self-Complementary Oligopeptide", Biopolymers, 1994, vol. 34, pp. 663-672.

Zhang et al., "Self-complementary oligopeptide matrices support mammalian cell attachment", Biomaterials, 1995, vol. 16, pp. 1385-1393.

International Search Report for Corresponding International Application No. PCT/JP2021/028175, 4 pages, Oct. 19, 2021.

Search Report for corresponding European Application No. 21850578. 2, issued on Sep. 12, 2025, 7 pages.

Anonymous: "UPI0001540AE9 | UniParc | UniProt", Jun. 19, 2007, XP093312258, Retrieved from the Internet: URL: http://www. uniprot.org/uniparc/UPI0001540AE9/entry, 4 pages.

\* cited by examiner

RIRGDMRADIR
(SEQ ID NO: 41)

RIRADMRGDIR
(SEQ ID NO: 42)

RIRGDIRGDIR
(SEQ ID NO: 43)

RIRGDIRADIR
(SEQ ID NO: 44)

RIRADIRGDIR
(SEQ ID NO: 45)

SELF-ASSEMBLING PEPTIDE

CROSS-REFERENCE TO RELATED APPLICATIONS

This application is a 371 of PCT/JP2021/028175, filed Jul. 29, 2021, which claims the benefit of Japanese Patent Application No. 2020-128805, filed Jul. 30, 2020 and Japanese Patent Application No. 2020-146597, filed Sep. 1, 2020.

REFERENCE TO A SEQUENCE LISTING SUBMITTED ELECTRONICALLY VIA EFS-WEB

The content of the electronically submitted sequence listing, file name: 522-1226_SequenceListing.txt; size: 20,051 bytes; and date of creation: Jan. 6, 2026 filed herewith, is incorporated herein by reference in its entirety.

TECHNICAL FIELD

The present invention relates to a self-assembling peptide, a gelling agent, a gelling composition comprising a gelling agent as an active ingredient, a composition for preparing a sustained-release gel, a sustained-release gel, and a method for producing a sustained-release gel.

BACKGROUND ART

Peptides (peptide gelling agents) capable of forming hydrogels have been used as biomaterials excellent in biocompatibility and biodegradability, for cell and tissue culturing, and have been recently applied to the fields of regenerative medicine. For example, applications as scaffold materials (artificial extracellular matrices, cell scaffold materials, and the like) for adhesion with cells, organs, and the like in vivo or in vitro, and as regenerative medicine materials for tissue regeneration are expected.

For example, gelatin and collagen extracted from animal cells, and matrigels derived from mouse sarcoma cells have been widely used as peptide gelling agents conventionally utilized, for cell and tissue culturing. However, animal-derived peptide gelling agents are not necessarily uniform in molecular weight distribution and component composition, and have differences in quality of each production lot. Additionally, in the case of introduction in vivo, the risk of causing allergy or unknown infection due to trace components or contaminations incorporated into extracts cannot also be avoided (Non-Patent Literatures 1 to 5).

Development of chemically synthesized low-molecular peptide gelling agents (synthetic low-molecular peptide gelling agents) as potent materials capable of overcoming the above problems of animal-derived peptide gelling agents is ongoing. Synthetic low-molecular peptide gelling agents can be synthesized as peptides having particular amino acid sequences, at high purities by solution synthesis or solid-phase synthesis methods. Therefore, there are advantages of stable quality of each production lot and of extremely reduced contaminations.

Known synthetic low-molecular peptide gelling agents include (i) an amphiphilic peptide in which one or two amino acids and an aromatic site (cinnamoyl group, Fmoc group, and the like) are linked, (ii) an amphiphilic peptide in which a long alkyl chain (palmitoyl group or the like) is linked to a terminus of a β-sheet forming peptide, and (iii) an amphiphilic peptide in which a hydrophilic amino acid and a hydrophobic amino acid are alternately linked (Non-Patent Literatures 6 to 7). The synthetic low-molecular peptide gelling agent corresponding to above (iii) does not comprise a non-natural backbone and can be composed only of natural amino acids, and thus is considered to be suitable particularly for clinical applications (Non-Patent Literatures 8 to 10).

However, synthetic low-molecular peptide gelling agents developed so far have problems of poor gelling in physiological conditions, and of high production cost due to large chain length. For providing a particular function to a peptide gelling agent, it is necessary to combine the peptide gelling agent with a biologically functional molecule such as a protein or to allow sustained release of the combined biologically functional molecule from the gel over a long period of time. For forming complexes with maintaining the activity of the biologically functional molecule, it is necessary to allow for gelling in physiological temperature and physiological pH conditions in which the biologically functional molecule does not denature.

For example, (RADA)$_4$ peptides (SEQ ID NO: 19) as representative examples of (iii) described above gel in acidic conditions, but do not gel in physiological pH conditions. In acidic conditions, most of biologically functional molecules such as proteins are denatured, and the activity is reduced or lost. Therefore, it is difficult to form complexes of a biologically functional molecule such as a protein with maintaining the activity in hydrogels formed by (RADA)$_4$ peptides (SEQ ID NO: 19), and availability as a material for regenerative medicine is limited. Furthermore, technologies for allowing sustained release of a complexed biologically functional molecule from a gel over a long period of time are not established.

Accordingly, there are needs for a synthetic low-molecular peptide gelling agent which can allow for hydrogel formation in physiological conditions and which has a relatively short chain length, and a sustained release technique based on it, for further extending availability as a material for regenerative medicine.

CITATION LIST

Non-Patent Literature

Non-Patent Literature 1: Vukicevic, S. et al., Experimental Cell Research, 1992, 202, 1-8.

Non-Patent Literature 2: Vallier, L. et al., Journal of Cell Science, 2005, 118, 4495-4509.

Non-Patent Literature 3: Cooperman, L. and Michaeli, D., Journal of the American Academy of Dermatology, 1984, 10, 638-646.

Non-Patent Literature 4: Lynn, A. K. et al., Journal of Biomedical Materials Research Part B Applied Biomaterials, 2004, 71, 343-354.

Non-Patent Literature 5: Scott, M. R. et al., Proceedings of the National Academy of Sciences of the United States of America, 1999, 96, 15137-15142.

Non-Patent Literature 6: Dasgupta, A. et al., RSC Advances, 2013, 3, 9117-9149.

Non-Patent Literature 7: Jonker, A. M. et al., Chemistry of Materials, 2012, 24, 759-773.

Non-Patent Literature 8: Zhang, S. et al., Proceedings of the National Academy of Sciences of the United States of America, 1993, 90, 3334-3338.

Non-Patent Literature 9: Zhang, S. et al., Biopolymers, 1994, 34, 663-672.
Non-Patent Literature 10: Zhang, S. et al., Biomaterials 1995, 16, 1385-1393.

SUMMARY OF INVENTION

Technical Problem

An object of the present invention is to provide a peptide gelling agent which gels in physiological conditions and which has a relatively short chain length, and a sustained-release gel based on it.

Solution to Problem

In order to solve the above problem, the present inventors have searched for an amphiphilic peptide in which a hydrophilic amino acid and a hydrophobic amino acid are alternately linked and which can gel at physiological temperature and in physiological pH conditions.

As a result, it has been found that an amphiphilic peptide in which particular hydrophilic amino acids and hydrophobic amino acids are alternately linked can form a gel in physiological conditions. As a result of further intensive studies, it has been found that the peptide has a dramatically high elastic modulus as compared with a conventional peptide gelling agent, and a gel formed by the peptide has extremely excellent sustained-release properties, and the present invention has been completed. The present invention is based on the novel findings described above, and provides the following [1] to [15] and (1) to (16).

[1] A hydrogelling self-assembling peptide comprising one or two core peptides consisting of an amino acid sequence represented by the following formula:

Xaa-Yaa-Zaa-Yaa-Xaa-Yaa-Zaa-Yaa-Xaa, wherein Xaa is independently Ile or Met, Yaa is independently Asp, Glu, Lys, or Arg, and Zaa is independently Ala or Gly, and wherein the full length of the amino acid sequence constituting said self-assembling peptide is 25 amino acids or less.

[2] The self-assembling peptide of [1], wherein the N-terminus and/or C-terminus of the self-assembling peptide is Arg.

[3] The self-assembling peptide of [1], wherein both of the two amino acids at the N-terminus and/or C-terminus of the self-assembling peptide are Arg.

[4] A fusion peptide formed by linking a functional peptide to the self-assembling peptide of any one of [1] to [3].

[5] The fusion peptide of [4], wherein said linking is mediated by covalent bonding or supramolecular interaction.

[6] The fusion peptide of [4] or [5], wherein the functional peptide is laminin, VEGF, or N-cadherin.

[7] A gelling agent consisting of the self-assembling peptide of any one of [1] to [3] or the fusion peptide of any one of [4] to [6].

[8] A gelling composition comprising the gelling agent of [7] as an active ingredient.

[9] The gelling composition of [8], comprising two or more of the gelling agents.

[10] An artificial extracellular matrix comprising the self-assembling peptide of any one of [1] to [3] or the fusion peptide of any one of [4] to [6], wherein the the self-assembling peptide or the fusion peptide is gelled.

[11] A method of gelling, comprising
maintaining the gelling agent of [7] or the gelling composition of [8] or [9] in a sol state, at a temperature not higher than the gelling temperature thereof in water or in an aqueous solution to thereby allow said gelling agent or said gelling composition to gel.

[12] The method of [11], wherein said temperature at which said gelling agent or said gelling composition is maintained in water or in the aqueous solution is in the range from 4 to 60° C.

[13] The method of [11] or [12], wherein said gelling agent or said gelling composition comprises any one or more negative ions selected from the group consisting of a hydrogen carbonate ion, a carbonate ion, a citrate ion, a tartrate ion, and a sulfate ion.

[14] The method of any one of [11] to [13], wherein said gelling agent or said gelling composition in a gel state has a pH of 6.0 to 8.0.

[15] The method of any one of [11] to [14], wherein the concentration of said gelling agent and/or said gelling composition is 0.4% by weight to 10% by weight.

(1) A composition for preparing a sustained-release gel, comprising a gelling agent consisting of a first self-assembling peptide, and a functional molecule formed by linking a second self-assembling peptide and a functional moiety,
wherein said first and second self-assembling peptides independently comprise one or two core peptides consisting of an amino acid sequence represented by the following formula:

Xaa-Yaa-Zaa-Yaa-Xaa-Yaa-Zaa-Yaa-Xaa, wherein Xaa is independently Ile or Met, Yaa is independently Asp, Glu, Lys, or Arg, and Zaa is independently Ala or Gly, and
wherein the full length of the amino acid sequence constituting said first and second self-assembling peptides is 25 amino acids or less, and
wherein said functional moiety is a functional peptide and/or a low molecular weight compound.

(2) The composition for preparing a sustained-release gel of (1), wherein the N-terminus and/or C-terminus of the first and/or second self-assembling peptide is Arg.

(3) The composition for preparing a sustained-release gel of (1), wherein both of the two amino acids at the N-terminus and/or C-terminus of the first and/or second self-assembling peptide are Arg.

(4) The composition for preparing a sustained-release gel of any one of (1) to (3), comprising two or more of the gelling agents.

(5) The composition for preparing a sustained-release gel of any one of (1) to (4), wherein said linking is mediated by covalent bonding or supramolecular interaction.

(6) The composition for preparing a sustained-release gel of any one of (1) to (5), wherein the functional peptide is selected from the group consisting of a vascular endothelial growth factor (VEGF), a fibroblast growth factor (FGF), and a hepatocyte growth factor (HGF).

(7) A sustained-release gel comprising the composition for preparing a sustained-release gel of any one of (1) to (6).

(8) A pharmaceutical composition comprising the sustained-release gel of (7).

(9) The pharmaceutical composition of (8), for use in transplantation.

(10) The pharmaceutical composition of claim (8) or (9), for promoting vascularization and/or suppressing neurodegeneration.

(11) The pharmaceutical composition of any one of (8) to (10), for use in treatment and/or prevention of nervous tissue damage and/or ischemia.

(12) The pharmaceutical composition of (11), wherein said nervous tissue damage is brain infarction.

(13) A method for producing a sustained-release gel, comprising:

a step of mixing the composition for preparing a sustained-release gel of any one of (1) to (6), with water or an aqueous solution; and a step of maintaining the mixture obtained after said mixing step, at a temperature not higher than the gelling temperature, to thereby allow the mixture to gel.

(14) The method according to (13), wherein any one or more negative ions selected from the group consisting of a hydrogen carbonate ion, a carbonate ion, a citrate ion, a tartrate ion, and a sulfate ion are further mixed in said mixing step.

(15) The method of claim (13) or (14), wherein said sustained-release gel in a gel state has a pH of 6.0 to 8.0.

(16) The method of any one of (13) to (15), wherein the concentration of the gelling agent in said sustained-release gel is 0.4% by weight to 10% by weight.

The present specification encompasses the disclosures of Japanese Patent Application Nos. 2020-128805 and 2020-146597 which serve as the basis for priority of the present application.

Advantageous Effects of Invention

According to the self-assembling peptide of the present invention, a peptide gelling agent which gels in physiological conditions and which has a relatively short chain length, and a sustained-release gel based on it can be provided.

BRIEF DESCRIPTION OF DRAWINGS

FIG. 8A illustrates a method of analyzing walking function before and after administration of a peptide gel to a mouse brain infarction model for evaluating the therapeutic effect. FIG. 8B shows the results of analyzing walking function before and after administration of a peptide gel to a mouse brain infarction model. The average value of the results in each condition is shown by a line. * represents the significant difference (P<0.05, student t-test) from administration of the P4 peptide gel alone.

FIG. 9E shows the volume of the damage core after peptide gel administration. FIG. 9F shows the volume of a penumbra region after peptide gel administration. The figure shows a box-whisker plot for the measurement results in seven animals. In the box-whisker plot, the lower end of a whisker, the lower end of a box, the line in a box, the upper end of a box, and upper end of a whisker respectively represent the minimum value, the first quartile, the median value, the third quartile, and the maximum value. It is noted that the minimum value and the maximum value are defined by the minimum value and the maximum value in the range of the first quartile—1.5× interquartile range (IQR) to the third quartile+1.5×IQR, and any observation value out of this range is plotted as an outlier.

FIG. 10E shows the number of laminin-positive cells in a penumbra region after peptide gel administration. FIG. 10F shows the number of EdU/laminin-co-positive cells in a penumbra region after peptide gel administration. The figure shows a box-whisker plot for the measurement results in seven animals. * represents the significant difference (P<0.05, student t-test) from administration of the P4 peptide gel alone.

FIG. 11D shows the number of FJC-positive cells in the penumbra region after peptide gel administration. * represents the significant difference (P<0.05, student t-test) from administration of the P4 peptide gel alone.

FIG. 12D shows the number of NeuN-positive cells in the penumbra region after peptide gel administration. * represents the significant difference (P<0.05, student t-test) from administration of the P4 peptide gel alone.

FIG. 13A shows the structure of the P4 peptide (RI-DARMRADIR, SEQ ID NO: 4). FIG. 13B shows the structure of the K(FAM)-G-P4 fusion peptide in which fluorescein is linked to the P4 peptide.

FIG. 14A shows the result of measuring an UV absorption spectrum of the K(FAM)-G-P4 fusion peptide released from the P4 peptide gel at each time point of 0, 1, 4, 24, and 72 hours. FIG. 14B shows the release rate (%) of the K(FAM)-G-P4 fusion peptide from the P4 peptide gel.

DESCRIPTION OF EMBODIMENTS

1. Self-Assembling Peptide and Fusion Peptide

1-1. Outline

Figure 1:
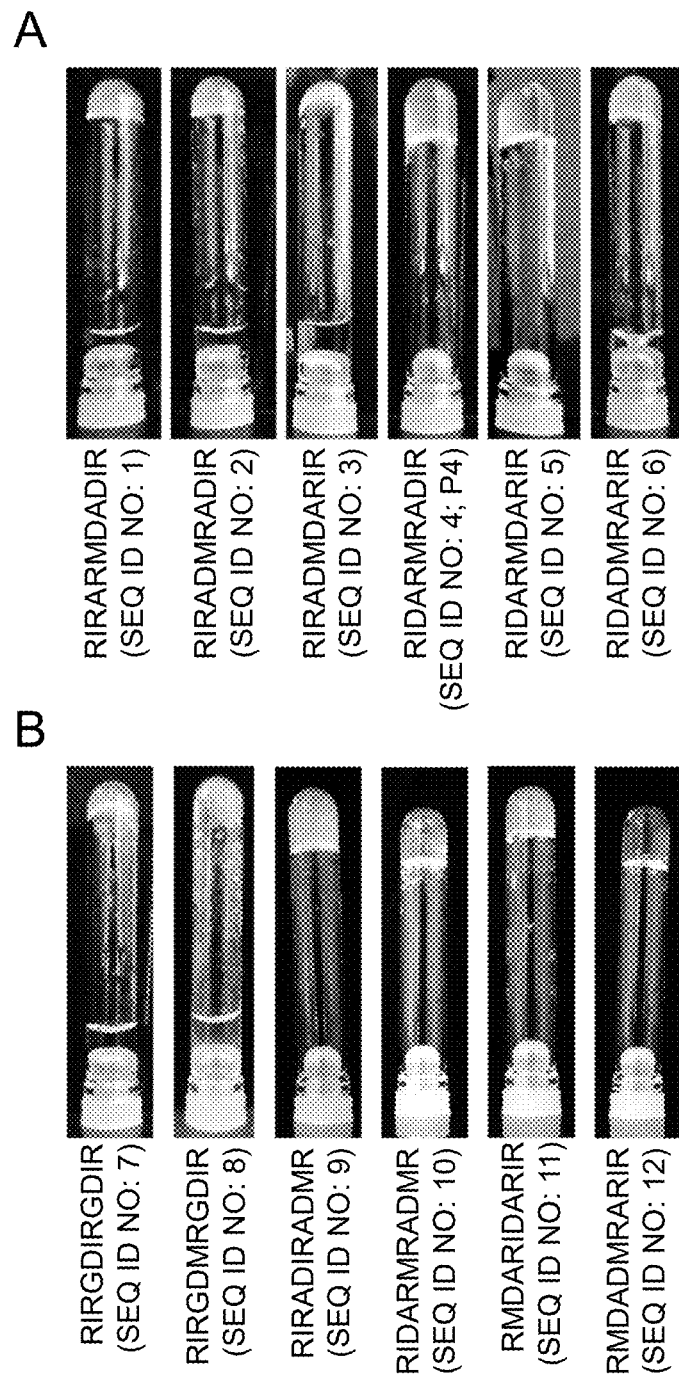
FIG. 1 shows the results of testing the gel formation ability of each peptide sample. In order to examine the fluidity of each peptide sample, a gel was formed on the bottom surface of a microtube and thereafter the microtube was vertically flipped, thereby testing whether the sample dropped to the cap side of the microtube. In the figure, the upper side of the photograph corresponds to the bottom of the microtube. In a case where a portion or all of the peptide sample remained on the bottom surface of the microtube, it was determined that the peptide sample gelled.

A first aspect of the present invention relates to a self-assembling peptide and a fusion peptide. The self-assembling peptide of the present aspect comprises a core peptide consisting of an amino acid sequence represented by formula: Xaa-Yaa-Zaa-Yaa-Xaa-Yaa-Zaa-Yaa-Xaa. Here, Xaa independently represents isoleucine (I/Ile) or methionine (M/Met), Yaa represents independently aspartic acid (D/Asp), glutamic acid (E/Glu), lysine (K/Lys), or arginine (R/Arg), and Zaa independently represents alanine (A/Ala) or glycine (G/Gly). The fusion peptide of the present aspect is a peptide formed by linking the self-assembling peptide of the present aspect to a functional peptide. The self-assembling peptide and the fusion peptide of the present aspect are capable of gelling in physiological conditions.

1-2. Definitions of Terms

The following terms frequently used herein are defined as follows.

The "self-assembling peptide" herein refers to a peptide which can be solidified in a unique temperature and pressure condition to become a gel state from a sol state dissolved in water or an aqueous solution. Examples include collagen (comprising glue, gelatin, and jelly), a (RADA)$_4$ peptide (SEQ ID NO: 19), and the like.

The "self-assembling" means that small molecules spontaneously assemble in a dispersion medium by intermolecular interaction or the like to form a three-dimensional steric structure. For example, sugar (polysaccharides such as starch and glucomannan), the above-mentioned collagen, and a high-absorbent polymer (sodium polyacrylate) self-assemble in water or an aqueous solution in a unique condition to form a fibrous mono-dimensional structure, which is further entangled to become a gel state having a three-dimensional steric structure. A substance which gels by self-assembling is herein often referred to as a "gelling agent". The self-assembling peptide of the present invention is one of gelling agents.

The "sol" refers to a colloidal particle which is dispersed in a dispersion medium in a liquid state having fluidity. Examples include colloids consisting of a gelling agent which are fluidized in a dispersion medium by increasing the temperature of a gel. The "colloid" refers to a state in which molecules or ions are aggregated to form a microparticle and are dispersed in a medium. A microparticle forming a colloid is called a "colloidal particle".

The "sol state" refers to a liquid state in which a colloidal particle is dispersed in a dispersion medium with fluidity. Examples include a state in which a gelling agent is dispersed in a dispersion medium such as water or an aqueous solution, and a state in which a gel is fluidized by increasing temperature.

The "solling (sol)" refers to a phase transition phenomenon from a gel state to a sol state.

The "gel" refers to a colloidal particle which is self-assembled in a dispersion medium, being solidified into a solid form by losing fluidity.

The "gel state" refers to a state in which a colloidal particle is self-assembled in a dispersion medium, being solidified by losing fluidity. In general, it is a state in which a sol is solidified by decreasing temperature.

The "gelling (gel)" refers to a phase transition phenomenon from a sol state to a gel state.

The "gelling temperature" herein refers to a temperature at which a gelling agent undergoes phase transition from a sol state to a gel state. The "solling temperature" herein refers to a temperature at which a gelling agent undergoes phase transition from a gel state to a sol state. The gelling temperature and the solling temperature of one gelling agent may be the same or different. It depends on the identity of the gelling agent whether the temperatures are the same or different.

The "peptide" herein refers to an amino acid polymer having one or more peptide bonds. The "peptide" is not limited by the number of amino acid residues comprised in a peptide. Accordingly, the "peptide" encompasses not only an oligopeptide comprising several amino acid residues, such as dipeptide or tripeptide, but also a polypeptide comprising many amino acid residues. Accordingly, not only a so-called protein, but also fragmented one, and one to which another peptide is linked by a peptide bond are also encompassed.

The "fusion peptide" herein refers to a self-assembling peptide of the present aspect which is linked to a functional peptide. The self-assembling peptide and the functional peptide may be linked by a covalent bonding or supramolecular interaction. The covalent bond is not limited, and examples thereof include a peptide bond and a disulfide bond. The "supramolecular interaction" herein means an intermolecular non-covalent interaction. Examples of a supramolecular interaction include hydrogen bonding, hydrophobic interaction or hydrophobic bonding, electrostatic interaction or ionic bonding, salt bridging, and coordinate bonding. A functional peptide is, without limitations, preferably linked to the N-terminus and/or the C-terminus of a self-assembling peptide, and furthermore a bond is preferably a covalent bond. A preferable covalent bond is a peptide bond.

The "functional peptide" herein refers to a peptide having a particular biological function in vivo or in vitro, or intracellularly or extracellularly. The "particular biological function" is herein not limited as long as it is a function capable of having any effect on a biomolecule such as a protein and a nucleic acid, a cell, a tissue or an individual. The particular biological function may be natural or non-natural, and examples include a cell adhesion function, a signaling function, a bonding function, a linking function, a labelling function, and a metabolic function. Examples of the linking function include a function of linking a biomolecule having a particular biological function, such as another peptide or a nucleic acid, a low molecular weight compound, or a metal ion. Examples include a function of mediating antigen/antibody bonding or receptor/ligand interaction, a function of binding a biomolecule such as RNA and/or DNA, and a function of binding a nickel ion or a copper ion. The labelling function includes a function of labelling a biomolecule such as a protein or a nucleic acid, a cell, a tissue, and an individual. Examples include fluorescent labelling and epitope tagging.

The "biocompatibility" herein refers to a property of allowing for introduction into a living body. In particular, the term refers to a property in which a certain material has no or if any extremely slight toxicity or adverse effect for a living body, and/or a property in which a certain material is not recognized as a foreign substance and is not eliminated in vivo. Herein, the "peptide having biocompatibility" refers to, for example, a peptide having no contamination derived from an organism and thus having no or very low risk of causing allergy and unknown infection to the human body. Examples of the peptide having biocompatibility include a chemically synthesized peptide.

The "living body" herein refers to a cell (comprising a cultured cell), a tissue, an organ, or an individual. Examples include, without limitations, a cell, a tissue or an organ derived from a human or an individual other than a human; or a cell or a tissue obtained by differentiation from a cell derived from a human or an individual other than a human, for example, a ES cell or iPS cell. A human-derived cell, a tissue or an organ consisting of human-derived cells, or a human individual are preferable.

The "physiological condition" herein refers to a condition such as temperature and pH in which the structure or activity of a biomolecule, the structure or function of a cell or a tissue, or the activity or survival of an individual is not substantially impaired. More specifically, a condition which can exist in vivo or in a cell is included. In particular, the "physiological condition" herein means a condition in which a biomolecule such as a protein is not denatured or is poorly denatured. Herein, the physiological pH is not limited as long as it is a pH at which a biomolecule such as a protein is not denatured or is poorly denatured. For example, the physiological pH is in the range from pH 4.0 to 10.0, in the range from pH 5.0 to 9.0, in the range from pH 6.0 to 8.0, or in the range from pH 6.5 to 7.5, for example, pH 7.4. Herein, the physiological temperature is not limited as long as it is a temperature at which a biomolecule such as a protein is not denatured or is poorly denatured. For example, the physiological temperature is a temperature in the range from 0 to 65° C., 4 to 60° C., 20 to 50° C., or 30 to 40° C., for example, 37° C.

The "amino acid" herein encompasses both a natural amino acid and a non-natural amino acid. A non-natural amino acid is, for example, an amino acid having any chemical modification group or substituent. The amino acid herein comprises any optical isomer, and may be any of a D-form or an L-form.

The "hydrophobic amino acid" herein refers to an amino acid having hydrophobicity or an amino acid with high hydrophobicity. Examples include alanine (Ala/A), glycine (Gly/G), proline (Pro/P), valine (Val/V), leucine (Leu/L), isoleucine (Ile/I), methionine (Met/M), cysteine (Cis/C), phenylalanine (Phe/F), tyrosine (Tyr/Y), and tryptophan (Trp/W).

The "hydrophilic amino acid" herein refers to an amino acid having hydrophilicity or an amino acid with high hydrophilicity. Examples include aspartic acid (Asp/D), glutamic acid (Glu/E), lysine (Lys/K), histidine (His/H), and arginine (Arg/R).

The "multiple (or plural)" herein refers to, for example, 2 to 10, 2 to 7, 2 to 5, 2 to 4, 2 to 3, or 2.

The "amino acid identity" herein refers to the proportion (%) of the number of identical amino acid residues in the entire number of amino acid residues in amino acid sequences of two peptides being compared, which are aligned by, if necessary, inserting a gap as appropriate into one of or both the peptides so that the number of identical amino acid residues becomes maximum. Such alignment of two amino acid sequences for calculation of the amino acid identity can be performed with known program such as Blast, FASTA, or ClustalW.

The "substitution (of amino acid)" herein refers to a substitution in the group of conservative amino acids which are similar in terms of characteristics such as charge, side chain, polarity, and aromatic properties, among 20 amino acids constituting a natural protein, unless particularly noted. Examples include a substitution in the uncharged polar amino acid group having a low-polarity side chain (Gly, Asn, Gln, Ser, Thr, Cys, Tyr), the branched amino acid group (Leu, Val, Ile), the neutral amino acid group (Gly, Ile, Val, Leu, Ala, Met, Pro), the neutral amino acid group having a hydrophilic side chain (Asn, Gln, Thr, Ser, Tyr, Cys), the acidic amino acid group (Asp, Glu), the basic amino acid group (Arg, Lys, His), and the aromatic amino acid group (Phe, Tyr, Trp). An amino acid substitution in these groups is known to hardly change peptide characteristics, and thus is preferable.

1-3. Configuration 1-3-1. Self-Assembling Peptide

The configuration of the self-assembling peptide of the present aspect is specifically described below.

The self-assembling peptide of the present aspect is constituted by a polypeptide comprising a core peptide consisting of an amino acid sequence selected based on a particular rule, or a polypeptide consisting of said core peptide.

The "core peptide" is herein a peptide of 9 amino acids constituting a portion or all of the self-assembling peptide of the present invention. In the present invention, the core peptide is a peptide formed by alternately linking a hydrophobic amino acid and a hydrophilic amino acid by a peptide bond, and the amino acid sequence thereof is selected based on a particular rule.

Specifically, the self-assembling peptide of the present aspect comprises a core peptide consisting of an amino acid sequence represented by the following formula:

Xaa-Yaa-Zaa-Yaa-Xaa-Yaa-Zaa-Yaa-Xaa, wherein Xaa is independently Ile or Met, Yaa is independently Asp, Glu, Lys, or Arg, and Zaa is independently Ala or Gly;

or consists of said core peptide.

In one embodiment, the self-assembling peptide of the present aspect comprises a core peptide consisting of an amino acid sequence represented by the following formula:

Xaa-Yaa-Zaa-Yaa-Xaa-Yaa-Zaa-Yaa-Xaa, wherein Xaa is independently Ile or Met, Yaa is independently Asp or Arg, and Zaa is independently Ala or Gly;

or consists of said core peptide.

The self-assembling peptide of the present aspect comprises one or more core peptides, or consists of one or more core peptides. For example, the self-assembling peptide of the present aspect may comprise one or two core peptides.

In a case where the self-assembling peptide of the present aspect comprises two core peptides, the two core peptides may consist of the same amino acid sequence, or may consist of different amino acid sequences.

In one embodiment, the self-assembling peptide of the present aspect may be those in which no additional amino acid residue is comprised at the N-terminal side and the C-terminal side of the core peptide, and in this case, the self-assembling peptide of the present aspect consists of only the core peptide. Examples of such a self-assembling peptide include IRARMDADI (SEQ ID NO: 28), IRADM-RADI (SEQ ID NO: 29), IRADMDARI (SEQ ID NO: 30), IDARMRADI (SEQ ID NO: 31), IDARMDARI (SEQ ID NO: 32), IDADMRARI (SEQ ID NO: 33), IRGDIRGDI (SEQ ID NO: 34), IRGDMRGDI (SEQ ID NO: 35), IRADI-RADM (SEQ ID NO: 36), IDARMRADM (SEQ ID NO: 37), MDARIDARI (SEQ ID NO: 38), MDADMRARI (SEQ ID NO: 39), IRGDMRADI (SEQ ID NO: 46), IRADMRGDI (SEQ ID NO: 47), IRGDIRGDI (SEQ ID NO: 48), IRGDIRADI (SEQ ID NO: 49), and IRADIRGDI (SEQ ID NO: 50).

In one embodiment, the self-assembling peptide of the present aspect may comprise a peptide consisting of one amino acid residue or multiple amino acid residues at the N-terminal side and/or the C-terminal side of the core peptide (hereinafter, respectively referred to as "N-terminal side peptide" or "C-terminal side peptide"). The amino acid residue(s) at the N-terminus and/or the C-terminus of the self-assembling peptide of the present aspect may be a hydrophilic amino acid. The N-terminal side peptide and/or C-terminal side peptide in the self-assembling peptide of the present aspect may each comprise one or more hydrophilic amino acids.

In one embodiment, the N-terminus and/or the C-terminus of the self-assembling peptide may be Arg. In other words, only the N-terminus of the self-assembling peptide of the present aspect may be Arg, only the C-terminus thereof may be Arg, or both the N-terminus and the C-terminus thereof may be Arg. Examples of such a self-assembling peptide include RIRARMDADIR (SEQ ID NO: 1), RIRADM-RADIR (SEQ ID NO: 2), RIRADMDARIR (SEQ ID NO: 3), RIDARMRADIR (SEQ ID NO: 4), RIDARMDARIR (SEQ ID NO: 5), RIDADMRARIR (SEQ ID NO: 6), RIRGDIRGDIR (SEQ ID NO: 7), RIRGDMRGDIR (SEQ ID NO: 8), RIRADIRADMR (SEQ ID NO: 9), RIDARM-RADMR (SEQ ID NO: 10), RMDARIDARIR (SEQ ID NO:

11), RMDADMRARIR (SEQ ID NO: 12), RIRGDM-RADIR (SEQ ID NO: 41), RIRADMRGDIR (SEQ ID NO: 42), RIRGDIRGDIR (SEQ ID NO: 43), RIRGDIRADIR (SEQ ID NO: 44), and RIRADIRGDIR (SEQ ID NO: 45).

In a further embodiment, both of the two amino acids at the N-terminus and/or the C-terminus of the self-assembling peptide may be Arg. In other words, only the N-terminus of the self-assembling peptide of the present aspect may be an Arg-Arg dipeptide, only the C-terminus thereof may be an Arg-Arg dipeptide, or both of the N-terminus and the C-terminus thereof may be an Arg-Arg dipeptide.

An amino acid constituting the self-assembling peptide of the present aspect, other than glycine, can be used regardless of the optical isomer. In other words, any of D-form or L-form may be used.

The full length of the amino acid sequence constituting the self-assembling peptide may be 25 amino acids or less. For example, the full length may be 20 amino acids or less, 15 amino acids or less, or 10 amino acids or less. More specifically, the full length may be 14 amino acids, 13 amino acids, 12 amino acids, 11 amino acids, 10 amino acids, or 9 amino acids.

In one embodiment, the self-assembling peptide of the present aspect consists of a core peptide, and the full-length of the amino acid sequence in this case is 9 amino acids.

In another embodiment, the self-assembling peptide of the present aspect is a peptide of 11 amino acids comprising a core peptide, and both of the N-terminus and the C-terminus may be Arg.

In still another embodiment, the self-assembling peptide of the present aspect is a peptide of 13 amino acids comprising a core peptide, and both of the N-terminus and the C-terminus may be an Arg-Arg dipeptide.

A modification group may be optionally added to an amino group of the N-terminal amino acid residue, and a carboxy group of the C-terminal amino acid residue of the self-assembling peptide of the present aspect. For example, an acetyl group may be added at the N-terminus of the self-assembling peptide of the present aspect. An $NH_2$ amide may also be added at the C-terminus of the self-assembling peptide of the present aspect.

1-3-2. Fusion Peptide

The fusion peptide of the present aspect is a peptide formed by linking a functional peptide to the self-assembling peptide of the present aspect. The linking between the self-assembling peptide and the functional peptide may be mediated by, for example, covalent bonding or supramolecular interaction. In one embodiment, the supramolecular interaction may be, for example, hydrogen bonding, hydrophobic interaction, electrostatic interaction, or coordinate bonding.

Examples of the fusion peptide of the present aspect include, without limitations, a peptide formed by linking a functional peptide at any position of the self-assembling peptide of the present aspect by a covalent bond such as a peptide bond or via a linker, but not limited thereto. The position at which the functional peptide is linked to the self-assembling peptide of the present aspect may be, for example, the N-terminus and/or the C-terminus of the self-assembling peptide. The self-assembling peptide of the present aspect being "linked to the N-terminus and/or C-terminus of the functional peptide by a peptide bond" encompasses all the cases of the self-assembling peptide of the present aspect being linked only to the N-terminus of the functional peptide, linked only to the C-terminus, and linked to both the N-terminus and the C-terminus. Additionally, the functional peptide may be linked to a side chain of an amino acid residue other than the N-terminus and the C-terminus of the self-assembling peptide of the present aspect.

The functional peptide constituting a fusion peptide of the present aspect is a peptide having a particular biological function in vivo or in a cell, as described above. Examples of the function include, but not limited to, a cell adhesion function, a signaling function, a bonding function, a linking function, a labelling function, or a metabolic function.

Further, the functional peptide constituting a fusion peptide of the present aspect can be selected depending on the intended use, and the purpose of the fusion peptide, for example, cell culturing, control of cell adhesion, growth, differentiation or the like, tissue or organ culturing, formation or regeneration, or vascularization induction.

Examples of the functional peptide in the present invention include, but not limited to, a cell adhesion molecule, an extracellular matrix molecule, a secretory protein, a binding protein, an enzyme, a marker protein, and an artificial peptide, and any peptide fragment thereof. The "cell adhesion molecule" here is a molecule involved in adhesion between cells or between a cell and an extracellular matrix on a cell surface. Examples include, but not limited to, cadherin such as N-cadherin, integrin, and selectin. The "extracellular matrix molecule" is a molecule constituting an extracellular matrix. Examples include, but not limited to, laminin, collagen, and fibronectin. The "secretory protein" is a protein to be produced intracellularly and secreted extracellularly. Examples include, but not limited to, a vascular endothelial growth factor (VEGF), a fibroblast growth factor (FGF), a hepatocyte growth factor (HGF), a platelet-derived growth factor (PDGF), and cytokine. The "binding protein" is a protein which specifically binds to a particular molecule. Examples include, but not limited to, an antibody or an antibody fragment, or an antigen, which mediates antigen/antibody bonding, (strept)avidin, a maltose-binding protein (MBP), a receptor or a ligand which mediates receptor/ligand interaction, a DNA-binding protein, and an RNA-binding protein. In particular, in a case where the functional peptide is a DNA-binding protein or an RNA-binding protein, a nucleic acid molecule to which the functional peptide binds can bind to another or multiple other nucleic acid molecules by formation of a multihelical structure or the like. The "marker protein" is a protein that can serve as a label in detecting a cell, a protein, and the like. Usually, a polypeptide by which the expression and presence of a protein of interest can be distinguished based on its activity is included. Examples include, but not limited to, a fluorescent protein such as GFP, a luminescent protein such as luciferin or aequorin, or an enzyme such as horseradish peroxidase (HRP) or alkaline phosphatase (AP). The "artificial peptide" is also referred to as "tag peptide", and is an oligopeptide consisting of several to dozens of amino acids artificially synthesized. Examples include epitope tags such as a FLAG tag, a histidine tag, an HA tag, and a DAP tag, and a His tag and a GST tag.

The self-assembling peptide or the fusion peptide of the present aspect may be optionally bound with one or more chemical modification groups. The structure of a chemical modification group is not particularly limited, and is a moiety confering a desired function to the self-assembling peptide or the fusion peptide bound thereto. Examples of the desired function include a labelling function, a linker function, a linking function, and a binding function. Examples of the chemical modification group confering a labelling function include a chromogenic group and a fluorescent group (for example, fluorescein). Examples of the chemical modification group confering a linker function include any polymer (for example, alkylene). Examples of the chemical modification group confering a binding function include a compound such as biotin. Examples of the chemical modification group which can be bound to the self-assembling peptide or the fusion peptide of the present aspect include lipid, sugar, aptamer, and a ligand of a receptor. Examples of the lipid can include cholesterol, a lipid such as a fatty acid (for example, vitamin E, vitamin A, vitamin D), a lipophilic vitamin such as vitamin K, an intermediate metabolite such as acyl CoA, a glycolipid, a glyceride, and a derivative thereof. Examples of the sugar include glucose and sucrose.

1-4. Effect

The self-assembling peptide of the present invention can gel in a physiological condition. For example, the self-assembling peptide can gel, for example, at a temperature in the range from 20 to 50° C. or in the range from 30 to 40° C. and at a pH in the range from pH 6.0 to 8.0 or in the range from pH 6.5 to 7.5, in a condition of 1 atm. Therefore, a gel can be formed without any loss of activity of a biomolecule such as a protein embedded in the gel, or at least partially retaining the activity.

Since the full length of the amino acid sequence of the self-assembling peptide of the present invention is 9 amino acids to 25 amino acids and has a relatively short chain length, it can be chemically synthesized in a large amount at a low cost. Since the self-assembling peptide can be synthesized at a high purity according to solution synthesis or solid-phase synthesis methods, it has advantages of stable quality in each production lot and of extremely low level of contamination.

The self-assembling peptide and the fusion peptide of the present aspect have biocompatibility, and can be introduced into a living body.

The self-assembling peptide and the fusion peptide of the present aspect can also be synthesized by use of a gene expression system. The "gene expression system" herein refers to an expression system capable of expressing a foreign gene in a host cell, or a cell-free gene expression system. For example, the self-assembling peptide and the fusion peptide of the present aspect can also be synthesized by introducing a nucleic acid encoding the self-assembling peptide and the fusion peptide of the present aspect into an autonomously replicable expression vector such as plasmid or Bacmid, and then introducing it into a host such as *E. coli*, an insect cell, or a cultured cell.

Further, a nucleic acid (for example, DNA) encoding a self-assembling peptide and a fusion peptide of the present aspect, an expression vector comprising the nucleic acid, and a host cell into which the expression vector is introduced are also provided.

2. Gelling Agent

2-1. Outline

A second aspect of the present invention relates to a gelling agent. The gelling agent of the present aspect consists of the self-assembling peptide or the fusion peptide of the first aspect. According to the gelling agent of the present aspect, phase transition from a gel state to a sol state, namely gelling, depending on temperature change is possible.

2-2. Configuration

The "gelling agent" in the present aspect is a gelling agent which is constituted by the self-assembling peptide or the fusion peptide of the first aspect and which can allow for gelling in a desired condition, for example a physiological condition, based on the difference in amino acid sequence.

Accordingly, a basic configuration of the gelling agent of the present aspect is substantially the same as in the content described in "1-3. Configuration" of the self-assembling peptide of the first aspect or the fusion peptide of the first aspect. Therefore, a specific description thereof is here omitted.

The pH of the gelling agent of the present aspect is not limited. For example, the pH is in the range from pH 4.0 to 10.0, in the range from pH 5.0 to 9.0, in the range from pH 6.0 to 8.0, or in the range from pH 6.5 to 7.5, for example, pH 7.4.

3. Gelling Composition

3-1. Outline

A third aspect of the present invention relates to a gelling composition. The gelling composition of the present aspect comprises the gelling agent described in the second aspect as an essential active ingredient, and additionally comprises a component for promoting gelling, a carrier, and the like. The gelling composition of the present aspect can be maintained in water or in an aqueous solution at a temperature equal to or lower than the gelling temperature to gel.

3-2. Configuration 3-2-1. Constituent Component

The gelling composition of the present invention is constituted by an active ingredient and a component other than the active ingredient. The component other than the active ingredient is not particularly limited, and examples include a component capable of promoting gelling of the gelling composition, and and a carrier. Hereinafter, each constituent component is specifically described.

(1) Active Ingredient

The gelling composition of the present aspect comprises one, or two or more of the gelling agents described in the second aspect, as an essential active ingredient. In other words, the self-assembling peptide and/or the fusion peptide of the first aspect are comprised. As an active ingredient, a single kind of, or a combination of two or more kinds of the gelling agent described in the second aspect may be used. For example, one kind of the self-assembling peptide and one kind of the fusion peptide of the first aspect can be combined.

The gelling composition of the present aspect can also encompass a drug or the like as other active ingredients. The "drug" herein has a concept of encompassing a low molecular weight compound, a peptide (comprising enzyme and antibody), or a nucleic acid (comprising an RNAi molecule such as miRNA, siRNA, and shRNA, an antisense nucleic acid, and an aptamer). The drug encompasses, without limitations, various types of drugs such as treatment medicine for the purpose of treatment of disease or the like, or symptom reduction, test medicine for detection or diagnosis of disease or the like, agricultural chemicals for the purpose of avoidance and/or extermination of pest insects and harmful animals, and antiseptic drugs for the purpose of virucidal action or sterilization. A single or two or more drugs may be comprised in the gelling composition of the present aspect.

The amount (content) of the gelling agent described in the second aspect incorporated to the gelling composition, is not particularly limited. The amount may be determined in consideration of the gelling condition as appropriate. In a case where the gelling composition of the present invention is administered in vivo, the amount may be appropriately determined depending on the type and/or the effective amount of the gelling agent comprised in the gelling composition, information on a subject, the dosage form of the gelling composition, and the type of a carrier or an additive described below. Specifically, the concentration of the gelling agent described in the second aspect in the gelling composition is not limited, and may be, for example, 0.4% by weight or more and 10% by weight or less, 1.0% by weight or more and 10% by weight or less, or may be, for example, 1.0% by weight or more and 2.0% by weight or less. The "effective amount" herein refers to an amount which is necessary for allowing the gelling agent in the gelling composition to exhibit a function as an active ingredient and which has almost no or no adverse effect on a living body to which the agent is applied. The effective amount can vary depending on various conditions such as information on a subject, the route of administration, and the number of doses. The "subject" herein refers to a living body as an application object of a pharmaceutical composition. For example, humans, domestic animals (cattle, horse, sheep, goat, pig, chicken, ostrich, and the like), racehorses, pet animals (dog, cat, rabbit, and the like), and laboratory animals (mouse, rat, guinea pig, monkey, marmoset, and the like) are included. Humans are preferable (in this case, particularly referred to as "subject"). The "information on a subject" encompasses various individual information on a living body to which the gelling composition is to be applied, for example, systemic health in the case of the subject, and the degree of progression, the degree of severity, age, weight, sex, dietary life, sensitivity to a drug, the presence of concurrent medication, and resistance to treatment in a case where the subject suffers from a disease/disease injury. A final effective amount of the gelling agent, and the amount of application, calculated based thereon are determined depending on, for example, information on an individual subject, finally by the discretion of a physician, a dentist, a veterinary physician, or the like.

(2) Component for Promoting Gelling

The gelling composition of the present aspect may comprise, if necessary, a component capable of promoting gelling. Examples of the component for promoting gelling include, but not limited to, a component having the effect of reducing the solubility of protein. This is because in general the component having the effect of reducing the solubility of a protein can promote gelling of the peptide gelling agent.

The component having the effect of reducing the solubility of protein is not limited, and examples include a positive ion and a negative ion having an effect of reducing the solubility of a protein. The positive ion and the negative ion each having the effect are well known as Hofmeister series by those skilled in the art. Examples of a negative ion include a hydrogen carbonate ion, a carbonate ion, a citrate ion, a tartrate ion, and a sulfate ion. Examples of a positive ion include a lithium ion, a sodium ion, a potassium ion, a magnesium ion, and a calcium ion.

The concentration of the positive ion and the negative ion having the effect of reducing the solubility of a protein is not particularly limited. For example, the concentration may be 1 mM or more, 5 mM or more, 10 mM or more, 20 mM or more, 30 mM or more, or 40 mM or more. In the case of using a hydrogen carbonate ion or a carbonate ion, the total concentration of a hydrogen carbonate ion and a carbonate ion may be 1 mM or more, 5 mM or more, 10 mM or more, 20 mM or more, 30 mM or more, or 40 mM or more, for example, 44 mM, considering that a hydrogen carbonate ion and a carbonate ion are usually in an equilibrium state in an aqueous solution.

(3) Carrier

The gelling composition of the present aspect can comprise, if necessary, a pharmaceutically acceptable carrier.

The "pharmaceutically acceptable carrier" herein refers to an additive usually used in the formulation art field. Examples include a solvent, an excipient, a filler, an emulsifier, a fluid additive modifier, a lubricant, and human serum albumin.

The solvent may be, for example, any of water or a pharmaceutically acceptable aqueous solution other than water, or a pharmaceutically acceptable organic solvent, and is preferably water or a pharmaceutically acceptable aqueous solution other than water. Examples of the aqueous solution include saline, an isotonic solution comprising glucose or other adjuvant, a phosphate buffer, a sodium acetate buffer, and any medium for use in cell culturing or tissue culturing. Examples of the adjuvant include D-sorbitol, D-mannose, D-mannitol, and sodium chloride, as well as a non-ionic surfactant at a low concentration, and polyoxyethylene sorbitan fatty acid ester. A commercially available medium may be used as the medium, and, for example, a DMEM medium, a Ham's F12 medium, a DMEM/F12 medium, a McCoy's 5A medium, an Eagle's MEM medium, an αMEM medium, an MEM medium, an RPMI1640 medium, an Iscove's modified Dulbecco's medium, an MCDB131 medium, a William's medium E, an IPL41 medium, or a Fischer's medium may be used.

Examples of the excipient include sugar such as monosaccharide, disaccharide, cyclodextrin and polysaccharide, a metal salt, citric acid, tartaric acid, glycine, polyethylene glycol, pluronic, kaolin, silicic acid, or any combination thereof.

Examples of the filler include vaseline, said sugar, and/or calcium phosphate.

Examples of the emulsifier include sorbitan fatty acid ester, glycerin fatty acid ester, sucrose fatty acid ester, and propylene glycol fatty acid ester.

Examples of the fluid additive modifier and the lubricant include silicate, talc, stearate or polyethylene glycol.

In addition to the above, if necessary, a solubilizer, a suspension agent, a diluent, a dispersant, a surfactant, a soothing agent, a stabilizer, a pH adjuster, an absorption promoter, a bulking agent, a humidity adding agent, a moisturizing agent, a wetting agent, an adsorbent, a taste improving and odor improving agent, a disintegration inhibitor, a coating agent, a colorant, a preserving agent, a preservative agent, an antioxidant, a perfume, a flavoring agent, a sweetener, a buffering agent, a tonicity agent, and/or the like usually used in a medicine can also be comprised as appropriate.

Such a carrier is used for mainly facilitating dosage form formation and maintaining the dosage form and the effect of drug, as well as making degradation of the gelling agent as an active ingredient by an enzyme in a living body difficult, and may be used as appropriate if necessary.

3-2-2. Property of the Gelling Composition

The pH of the gelling composition of the present aspect is not limited. For example, the pH may be a physiological pH, and is in the range from pH 4.0 to 10.0, in the range from pH 5.0 to 9.0, in the range from pH 6.0 to 8.0, or in the range from pH 6.5 to 7.5, for example, pH 7.4.

The gelling composition of the present aspect can be maintained in water or in an aqueous solution at a temperature equal to or lower than the gelling temperature to gel.

The gelling temperature is in principle based on that of the self-assembling peptide or the fusion peptide constituting the gelling agent as an active ingredient. Accordingly, the gelling composition of the present aspect can gel, for example, under a condition of 1 atm at a temperature in the range from 4 to 80° C., in the range from 10 to 70° C., in the range from 15 to 60° C., in the range from 20 to 50° C. or in the range from 30 to 40° C., for example, 37° C.

In a case where the gelling composition of the present aspect comprises a fusion peptide, the gelling composition can gel in a physiological condition without any substantial loss of activity of the functional peptide constituting the fusion peptide, or at least partially retaining the activity. Therefore, the function based on a biological function of the functional peptide constituting the fusion peptide can be exhibited after gelling of the gelling composition of the present aspect. For example, in a case where VEGF is used as a functional peptide, the gelling composition after gelling can be transplanted in vivo according to a surgical method or the like, to thereby induce angiogenesis in the gel.

The gelling composition of the present aspect can be used as an artificial extracellular matrix in vivo or in vitro. Also in the case, the function based on a biological function of the functional peptide constituting the fusion peptide can be exhibited after gelling of the gelling composition of the present aspect. As a functional peptide, for example, an extracellular matrix molecule such as laminin or N-cadherin can be used. The gelling composition after gelling in the body, when used as an artificial extracellular matrix, can allow for control of cell adhesion, growth, differentiation or the like, and tissue or organ formation, regeneration or the like, in the gel.

The gelling composition of the present aspect, which is introduced into a subject, can also be removed from a transplantation site by incising a target site according to surgery or the like after control of cell adhesion, growth, differentiation or the like, and tissue or organ formation, regeneration or the like are sufficiently achieved at the administration site.

3-2-3. Dosage Form

The dosage form of the gelling composition of the present aspect is not particularly limited. For example, a solid agent which can be introduced into a target site may be used. In the case of a solid agent, the shape is not limited. It may be a general solid dosage form such as a dust formulation, a powder, a granule or a tablet, or may be in the form of a material for transplantation. The solid agent is a solid, and thus the gelling composition as the solid agent is usually in a gel state.

3-2-4. Application Method

The method for applying the gelling composition of the present aspect is not particularly limited, and is preferably parenteral administration, further preferably topical administration. Examples of the topical administration include intramuscular administration, subcutaneous administration, tissue administration, and organ administration. In a case where the gelling composition of the present aspect is topically administered, the gelling composition of the present aspect, as it is in a gel state, may be introduced into a target site. For example, the gelling composition, as it is in a gel state, can be transplanted by incising a target site according to surgery. The dose may be an effective amount to produce response to an active ingredient. The effective amount can be appropriately selected depending on information on a subject.

3-2-5. Removal Method

The gelling composition of the present aspect can be, if necessary, removed from an administration site. For example, the gelling composition, as it is in a gel state, can be surgically removed by incising the administration site according to surgery.

4. Artificial Extracellular Matrix

4-1. Outline

A fourth aspect of the present invention relates to an artificial extracellular matrix. The artificial extracellular matrix of the present aspect is constituted by the gelling agent described in the second aspect, or the gelling composition described in the third aspect. The artificial extracellular matrix of the present aspect can be used either in vitro or in vivo. The artificial extracellular matrix of the present aspect, when it comprises a fusion peptide, can retain activity of the functional peptide constituting the fusion peptide.

4-2. Configuration

The "artificial extracellular matrix" herein refers to a scaffold material for cell culturing or tissue regeneration, and refers to a material which can allow for control of cell adhesion, growth, differentiation or the like, and culturing, formation, regeneration or the like of a transplanted cell, a transplanted tissue or a transplanted organ. The artificial extracellular matrix may be used in vitro, or may be used in vivo.

The "control of cell adhesion, growth, differentiation or the like" herein refers to promotion and/or suppression of cell adhesion, growth or differentiation.

The artificial extracellular matrix of the present aspect is constituted by the gelling agent described in the second aspect, or the gelling composition described in the third aspect. Accordingly, the basic configuration in the present aspect is substantially the same as the configuration of the gelling agent of the second aspect or the gelling composition of the third aspect.

The artificial extracellular matrix of the present aspect is in principle a gelling agent in a gel state. This is because a certain rigidity for cell anchoring is necessary for a function as a scaffold for a cell and a liquid sol cannot usually achieve the purpose.

In a case where the artificial extracellular matrix of the present aspect comprises a fusion peptide, the functional peptide constituting the fusion peptide is, for example, a molecule which controls cell adhesion, growth, differentiation or the like, or a molecule which controls tissue or organ formation, regeneration or the like. Examples include a cell adhesion molecule, an extracellular matrix molecule, a secretory protein, a binding protein, an enzyme, a marker protein and an artificial peptide, and any peptide fragment thereof. The functional peptide constituting the fusion peptide which can be comprised in the artificial extracellular matrix of the present aspect is preferably a cell adhesion molecule or an extracellular matrix molecule, and is, for example, laminin or N-cadherin.

4-3. Effect

The artificial extracellular matrix of the present aspect can allow for control of cell adhesion, growth, differentiation or the like, or tissue or organ formation, regeneration or the like, in vitro or in vivo.

An aspect of use of the artificial extracellular matrix of the present aspect in vivo is described in the "3-2. Configuration" in the "3. Gelling composition", and a specific description thereof is omitted here.

In the case of using the artificial extracellular matrix of the present aspect, the shape of the artificial extracellular matrix can be processed depending on an desired shape of a cell, a tissue or an organ of interest. For example, the artificial extracellular matrix of the present invention can be formed by pouring it in a sol state into a mold, and gelling. Alternatively, the artificial extracellular matrix of the present invention can also be formed into a shape of interest by partially making a gel into a sol by local heat treatment.

5. Method of Gelling

5-1. Outline

A fifth aspect of the present invention relates to a method of gelling the gelling agent or the gelling composition of the present invention.

5-2. Method 5-2-1. Step

The method of gelling of the present invention comprises, as an essential step, maintaining the gelling agent or the gelling composition of the present invention, which is in a sol state, in water or in an aqueous solution at a temperature equal to or lower than the gelling temperature. The present step can allow for phase transition of the gelling agent or the gelling composition of the present invention from a sol state to a gel state.

The temperature used in the present step varies depending on the type of the gelling agent or the gelling composition used, and thus may be determined as appropriate depending on the type. For example, the gelling agent or the gelling composition of the present invention may be maintained at a temperature in the range from 4 to 80° C., in the range from 10 to 70° C., in the range from 15 to 60° C., in the range from 20 to 50° C. or in the range from 30 to 40° C., for example, 37° C. In particular, in a case where the artificial extracellular matrix of the present aspect comprises a fusion peptide, the temperature condition where the activity of the functional peptide constituting the fusion peptide is not lost or the activity at least partially remains is preferable, and, for example, a temperature condition in the range from 4 to 80° C., in the range from 10 to 70° C., in the range from 15 to 60° C., in the range from 20 to 50° C., or in the range from 30 to 40° C., for example, 37° C. can be used.

The method for controlling the temperature used in the present step is not particularly limited, and a known method may be used. Examples include a method comprising placing the gelling agent or the gelling composition in a thermoregulated bath or the like.

The gelling agent or said gelling composition to be subjected to the present step may comprise a component capable of promoting gelling. Examples of a component for promoting gelling that can be used include, without limitations, a component having an effect of reducing the solubility of a protein. Examples of the negative ion having the effect include a hydrogen carbonate ion, a carbonate ion, a citrate ion, a tartrate ion, and a sulfate ion. Examples of the positive ion having the effect include a lithium ion, a sodium ion, potassium ion, a magnesium ion, and a calcium ion. The concentration of the above component is not particularly limited. For example, the concentration may be 1 mM or more, 5 mM or more, 10 mM or more, 20 mM or more, 30 mM or more, or 40 mM or more. In the case of using a hydrogen carbonate ion or a carbonate ion, the total concentration of a hydrogen carbonate ion and a carbonate ion may be 1 mM or more, 5 mM or more, 10 mM or more, 20 mM or more, 30 mM or more, or 40 mM or more, for example, 44 mM or more, considering that a hydrogen carbonate ion and a carbonate ion are usually in an equilibrium state in an aqueous solution.

The pH of the gelling agent or said gelling composition in a gel state to be subjected to the present step is not limited. For example, the pH is in the range from pH 4.0 to 10.0, in the range from pH 5.0 to 9.0, in the range from pH 6.0 to 8.0, or in the range from pH 6.5 to 7.5, for example, pH 7.4.

The concentration of the gelling agent, or the gelling agent comprised in said gelling composition, to be subjected to the present step, is not limited, and may be, for example, 0.4% by weight or more and 10% by weight or less, or 1.0% by weight or more and 10% by weight or less, and may be, for example, 1.0% by weight or more and 2.0% by weight or less.

6. Composition for Preparing a Sustained-Release Gel

6-1. Outline

A sixth aspect of the present invention relates to a composition for preparing a sustained-release gel. The composition for preparing a sustained-release gel of the present invention comprises a gelling agent and a functional molecule as essential active ingredients, and additionally comprises a component for promoting gelling, a carrier, and the like. The composition for preparing a sustained-release gel of the present aspect can allow for gel formation with the activity of the functional molecule being maintained in a physiological condition and furthermore sustained release of the functional molecule.

6-2. Definitions of Terms

The "sustained release" herein refers to gradual release of a substance into a space. In particular, the term herein refers to gradual diffusion of a substance comprised in a gel, from the gel. For example, the term refers to diffusion at a rate lower than the rate of diffusion of the substance not comprised in a gel. In a case where the functional molecule undergoes sustained release from a gel embedded in vivo, the functional molecule is present in a space around the gel (for example, a disease site, a damaged site, a tissue or an organ to which the gel is embedded) over a long period of time, and the function thereof is provided.

The "long period" or "long period of time" herein means a period longer than the period during which a substance is continuously diffused under normal conditions. Specifically, the term means a period longer than the period during which a substance not contained in a gel is continuously diffused under the same conditions. A specific period varies depending on the type of a substance, and a period of, for example, 1 hour or more, 2 hours or more, 3 hours or more, 6 hours or more, half a day or more, one day or more, two days or more, three days or more, one week or more, two weeks or more, one month or more, two months or more, three months or more, four months or more, six months or more, or one year or more is included.

The "vascular endothelial growth factor (VEGF)" is a group of glycoprotein involved in angiogenesis and vascularization. VEGF generally functions as a homodimer. VEGF encompasses an isoform thereof, such as VEGF-A, VEGF-B, VEGF-C, VEGF-D, VEGF-E, a placental growth factor-1 (PlGF-1), PlGF-2, and a splicing variant thereof. Four splicing variants, VEGF121, VEGF165, VEGF189, and VEGF206, are known as human VEGF-A isoforms.

The "fibroblast growth factor (FGF)" is herein a peptide having various functions, such as functions in development, vascularization, and wound healing. Twenty-two types of FGF, FGF1 to FGF14 and FGF16 to FGF23, are known in human.

The "hepatocyte growth factor (HGF)" is herein a peptide having a wide variety of activities, such as cell growth, anti-cell death, and vascularization.

6-3. Configuration

The composition for preparing a sustained-release gel of the present invention is constituted by an active ingredient and a component other than the active ingredient. The component other than the active ingredient is not particularly limited, and examples comprise a component which can promote gelling of the composition for preparing a sustained-release gel, a carrier, and other drugs. Hereinafter, each constituent component is specifically described.
(1) Active Ingredient The composition for preparing a sustained-release gel of the present invention comprises a gelling agent and a functional molecule.

The configuration of the gelling agent comprised in the composition for preparing a sustained-release gel of the present invention is in accordance with the configuration of the gelling agent consisting of the self-assembling peptide in the second aspect. Accordingly, the configuration of the self-assembling peptide (hereinafter referred to as "first self-assembling peptide") constituting the gelling agent is in accordance with the configuration of the self-assembling peptide of the first aspect.

The functional molecule comprised in the composition for preparing a sustained-release gel of the present invention is a molecule obtained by linking the self-assembling peptide (hereinafter referred to as "second self-assembling peptide," distinguished from the first self-assembling peptide) and a functional moiety. The configuration of the second self-assembling peptide is also in accordance with the configuration of the self-assembling peptide of the first aspect.

The amino acid sequences of the first and second self-assembling peptides are selected independently from each other. Accordingly, the amino acid sequences may be the same or different.

Specifically, in the composition for preparing a sustained-release gel of the present invention, the first self-assembling peptide constituting the gelling agent and the second self-assembling peptide comprised in the functional molecule independently comprise one or two core peptides consisting of an amino acid sequence represented by the following formula:

$$\text{Xaa-Yaa-Zaa-Yaa-Xaa-Yaa-Zaa-Yaa-Xaa,}$$

wherein Xaa is independently Ile or Met, Yaa is independently Asp, Glu, Lys, or Arg, and Zaa is independently Ala or Gly;

and the full length of an amino acid sequence constituting the first and second self-assembling peptides is 25 amino acids or less.

The composition for preparing a sustained-release gel of the present invention may comprise two or more gelling agents. In other words, the composition for preparing a sustained-release gel of the present invention may comprise two or more different self-assembling peptides as the first self-assembling peptide.

The second self-assembling peptide and the functional moiety in the functional molecule described above may be linked by covalent bonding or supramolecular interaction. The covalent bonding and the supramolecular interaction are in accordance with the description of the first aspect. The functional moiety is, without limitations, preferably linked to the N-terminus and/or the C-terminus of the second self-assembling peptide, and furthermore the bond is preferably a covalent bond. The covalent bond is, for example, a peptide bond.

The functional moiety comprised in the functional molecule in the composition for preparing a sustained-release gel of the present invention is a functional peptide and/or a low molecular weight compound. The functional peptide here is in accordance with the description of the first aspect. The functional peptide is not limited, and may be, for example, a vascular endothelial growth factor (VEGF), a fibroblast growth factor (FGF), and/or a hepatocyte growth factor (HGF).

VEGF may be any of any peptide belonging to the VEGF family, or a variant, an isoform, a mutant or a peptide fragment thereof. Examples of any peptide belonging to the VEGF family include VEGF-A, VEGF-B, VEGF-C, VEGF-D, VEGF-E, PlGF-1, and PlGF-2. In particular, in a case where VEGF is VEGF-A, VEGF-A encompasses at least four splicing isoforms which are present, VEGF121, VEGF165, VEGF189, and VEGF206, and may be any of the four isoforms.

The species from which VEGF is derived is not limited. Accordingly, VEGF may be a human VEGF, and a VEGF orthologue of species other than human, for example, a VEGF orthologue of mammal species such as mouse, rat, rabbit, cattle, cynomolgus, and marmoset.

In one embodiment, VEGF is a human VEGF165 or a VEGF165 orthologue. Examples of the human VEGF165 include hVEGFA165 consisting of an amino acid sequence represented by SEQ ID NO: 27, and a SNP variant thereof. Examples of the VEGF165 orthologue include, but not limited to, a mouse orthologue mVegfa164 consisting of an amino acid sequence represented by SEQ ID NO: 40.

A mutant or a peptide fragment of VEGF preferably has VEGF activity (for example, an an activity of promoting vascularization and/or an activity of suppressing neurodegeneration) equal to or more than that of VEGF. Examples of the mutant of VEGF165 include a VEGF165 mutant consisting of an amino acid sequence represented by SEQ ID NO: 27 or SEQ ID NO: 40, in which one or multiple amino acids are deleted, substituted or added, or an amino acid sequence having an identity of 60% or more, 70% or more, 80% or more, 85% or more, 90% or more, 95% or more, or 99% or more with the amino acid sequence represented by SEQ ID NO: 27 or SEQ ID NO: 40.

FGF may be any of any peptide belonging to the FGF family (for example, FGF1 to FGF14 and FGF16 to FGF23), or a variant, an isoform, a mutant or peptide fragment thereof. The species from which FGF is derived is not limited. Accordingly, FGF may be a human FGF (for example, hFGF2 consisting of an amino acid sequence represented by SEQ ID NO: 21), or an FGF orthologue of any organism species (for example, mammal species) other than human. A mutant or a peptide fragment of FGF preferably has FGF activity (for example, an activity of promoting vascularization and/or an activity of suppressing neurodegeneration) equal to or more than that of FGF.

HGF is not particularly limited, and HGF may be any of variant, isoform, mutant or peptide fragment. The species from which HGF is derived is not limited. Accordingly, HGF may be a human HGF (for example, hHGF consisting of an amino acid sequence represented by SEQ ID NO: 22), or an HGF orthologue of species (for example, mammal species) other than human. A mutant or a peptide fragment of HGF preferably has HGF activity (for example, an activity of promoting vascularization and/or an activity of suppressing neurodegeneration) equal to or more than that of HGF.

The amount (contents) of the gelling agent and the functional molecule comprised in the composition for preparing a sustained-release gel are not particularly limited. The amount may be determined as appropriate in consideration of the gelling condition and the application of the sustained-release gel. In a case where the composition for preparing a sustained-release gel of the present invention is administered in vivo, the type and/or the effective amount of the gelling agent and the functional molecule comprised in the composition for preparing a sustained-release gel may be determined as appropriate depending on information of a subject, the dosage form of the composition for preparing a sustained-release gel, and the type of a carrier or an additive described below. Specifically, the concentration of the gelling agent comprised in the composition for preparing a sustained-release gel is not limited, and may be, for example, 0.4% by weight or more and 10% by weight or less, 1.0% by weight or more and 10% by weight or less, or may also be, for example, 1.0% by weight or more and 2.0% by weight or less. The concentration of the functional molecule comprised in the composition for preparing a sustained-release gel is not limited, and may be $1/100,000$ to $1/100$, or $1/10,000$ to $1/1,000$ of the concentration of gelling agent, and may be, for example, $1 \times 10^{-6}$% by weight or more and 0.1% by weight or less, $1 \times 10^{-5}$% by weight or more and $1 \times 10^{-2}$% by weight or less, or $1 \times 10^{-4}$% by weight or more and $1 \times 10^{-3}$% by weight or less.

(2) Component for Promoting Gelling, Carrier, and Other Drugs

The composition for preparing a sustained-release gel of the present invention can comprise, if necessary, a component capable of promoting gelling (a component for promoting gelling), a pharmaceutically acceptable carrier, and/or other drugs. The component for promoting gelling and the carrier are in accordance with the third aspect.

Other drugs are not particularly limited, and examples include a drug having the same pharmacological effect as that of the functional molecule, and an antibiotic.

The dosage form, the application method, and the removal method of the composition for preparing a sustained-release gel of the present invention are in accordance with "3-2-3. Dosage form," "3-2-4. Application method," and "3-2-5. Removal method" in the third aspect.

6-4. Effect

The composition for preparing a sustained-release gel of the present aspect can gel in a physiological condition which does not impair the activity of the functional molecule, and furthermore can allow for sustained release of the functional molecule from the gel. The gel prepared from the composition for preparing a sustained-release gel of the present aspect has a high efficiency of incorporating the functional molecule and has an excellent property of sustained-release.

7. Sustained-Release Gel

7-1. Configuration

A seventh aspect of the present invention is a sustained-release gel.

The sustained-release gel of the present aspect comprises water or an aqueous solution, in addition to the configuration of the composition for preparing a sustained-release gel described in the sixth aspect. Accordingly, the basic configuration of the sustained-release gel of the present aspect, except for water or an aqueous solution, is substantially the same as the configuration of the composition for preparing a sustained-release gel described in the sixth aspect.

The pH of the sustained-release gel of the present aspect is not particularly limited, and is, for example, in the range from pH 4.0 to 10.0, in the range from pH 5.0 to 9.0, in the range from pH 6.0 to 8.0, or in the range from pH 6.5 to 7.5, for example, pH 7.4. The pH of the sustained-release gel of the present aspect is preferably a pH which does not cause loss of activity of the functional molecule comprised in the gel, or which maintains at least part of the activity.

The concentration of the gelling agent comprised in the sustained-release gel of the present aspect is not particularly limited, and may be, for example, 0.4% by weight or more and 10% by weight or less, or 1.0% by weight or more and 10% by weight or less, or may be, for example, 1.0% by weight or more and 2.0% by weight or less.

7-2. Effect

The sustained-release gel of the present aspect can comprise the functional molecule without any loss of the activity thereof, and can continue to release the functional molecule over a long period of time.

The shape of the sustained-release gel of the present aspect is easily processed. For example, the shape of the sustained-release gel can be processed in accordance with the location where the gel is to be embedded in vivo (for example, a disease site or a damaged site).

8. Pharmaceutical Composition

8-1. Configuration

An eighth aspect of the present invention relates to a pharmaceutical composition. The pharmaceutical composition of the present aspect comprises the sustained-release gel of the seventh aspect. Accordingly, the configuration of the pharmaceutical composition of the present aspect, except for the following configuration, is in accordance with the sixth to seventh aspects. The functional peptide comprised in the functional molecule in the pharmaceutical composition of the present invention is, for example, VEGF, FGF, and/or HGF.

In one embodiment, the pharmaceutical composition of the present invention is for transplantation. The pharmaceutical composition of the present invention can be transplanted, for example by surgically incising a target site.

Further, the pharmaceutical composition of the present invention can be used for promoting vascularization and/or suppressing neurodegeneration.

A target disease of the pharmaceutical composition of the present invention is not particularly limited. This is because a functional peptide or a low molecular weight compound effective for treatment and/or prevention of disease can be used as the functional moiety of the functional molecule comprised in the pharmaceutical composition of the present invention, to thereby provide a sustained-release pharmaceutical composition effective for treatment and/or prevention of any disease. Specific examples of the target disease include, but not limited to, nervous tissue damage and/or ischemia.

The "nervous tissue damage" herein encompasses both central nervous tissue damage and peripheral nervous tissue damage.

The central nervous tissue damage includes brain damage and spinal cord damage. The brain damage is, for example, traumatic brain damage or cerebral vascular disease. The cerebral vascular disease encompasses both brain infarction (ischemic cerebral vascular disease) and cerebral hemorrhage. The spinal cord damage is, for example, cervical cord damage, thoracic cord damage, lumbar cord damage, or sacral cord damage.

The peripheral nervous tissue damage encompasses damage of any peripheral nervous tissue. Examples include damage of motor nerves, sensory nerves, and autonomic nerves.

The "ischemia" is herein ischemia in any organ or tissue. Examples include lower-limb ischemia (for example, arteriosclerosis obliterans, and a critical type thereof, which is critical lower-limb ischemia), ischemic cardiac disease (for example, cardiac infarction), and the above cerebral vascular diseases.

The treatment herein is not limited, and encompasses radical treatment and preventive treatment. The prevention herein encompasses prevention of development, prevention of progression, and prevention of recurrence.

8-2. Effect

The pharmaceutical composition of the present invention can be transplanted to a disease site, a damaged site or an ischemic site of a subject, or a vicinity site thereof to thereby allow the functional molecule such as VEGF to be released in a sustained manner over a long period of time, resulting in promotion of vascularization and suppression of neurodegeneration. Alternatively, the pharmaceutical composition of the present invention can also be transplanted to a particular site in the body of a subject to thereby allow sustained release of the functional molecule throughout the body over a long period of time.

Accordingly, the pharmaceutical composition of the present invention can allow the function of the functional peptide and the low molecular weight compound comprised in the functional molecule to be produced in vivo for a longer period, resulting in an increased treatment effect.

The risk of cerebral vascular disease can be detected by an imaging test such as CT test or MRI test, and the development thereof can be prevented by the pharmaceutical composition of the present invention. While a cerebral vascular disease such as brain infarction is highly recurrent, the recurrence can also be prevented by the pharmaceutical composition of the present invention.

9. Method for Producing a Sustained-Release Gel

9-1. Outline

A ninth aspect of the present invention is a method for producing a sustained-release gel. The method for producing a sustained-release gel of the present aspect can produce a sustained-release gel comprising a functional molecule or a functional moiety maintaining at least part of the activity.

9-2. Step

The method for producing a sustained-release gel of the present invention comprises a step of mixing the composition for preparing a sustained-release gel of the sixth aspect with water or an aqueous solution (mixing step), and a step of maintaining the mixture obtained after the mixing step, at a temperature not higher than the gelling temperature to thereby allow the mixture to gel (gelling step), as essential steps.

A component capable of promoting gelling in the gelling step may be further mixed in the mixing step. The configuration of such a component for promoting gelling is in accordance with the third aspect, and the description thereof is omitted here.

The temperature used in the gelling step, the method for controlling the temperature used in the gelling step, the pH of the gel in a gel state, and the concentration of the gelling agent in the sustained-release gel are in accordance with the fifth aspect.

EXAMPLES

Example 1: Fluidity Test for Peptide Samples (Purpose)

A self-assembling peptide which gels in a physiological condition is to be developed.

(Method)

(1) Chemical Synthesis of Peptides

Eighteen types of peptides in total: RIRARMDADIR (SEQ ID NO: 1), RIRADMRADIR (SEQ ID NO: 2), RIRADMDARIR (SEQ ID NO: 3), RIDARMRADIR (SEQ ID NO: 4), RIDARMDARIR (SEQ ID NO: 5), RIDADMRARIR (SEQ ID NO: 6), RIRGDIRGDIR (SEQ ID NO: 7), RIRGDMRGDIR (SEQ ID NO: 8), RIRADIRADMR (SEQ ID NO: 9), RIDARMRADMR (SEQ ID NO: 10), RMDARIDARIR (SEQ ID NO: 11), RMDADMRARIR (SEQ ID NO: 12), RVRVRVDVDVR (SEQ ID NO: 13), RVRVDVRVDVR (SEQ ID NO: 14), RVRVDVDVRVR (SEQ ID NO: 15), RVDVRVRVDVR (SEQ ID NO: 16), RVDVRVDVRVR (SEQ ID NO: 17), and RVDVDVRVRVR (SEQ ID NO: 18) were each synthesized at a scale of 0.10 mmol by following method according to the Fmoc peptide solid-phase synthesis method using a polystyrene resin. An acetyl group is bound to the N-terminus of the synthesized peptide, and the C-terminus is NH$_2$ amide.

A Fmoc-NH-SA resin (Watanabe Chemical Industries, Ltd.) (250 mg, 0.10 mmol) was immersed in N,N'-dimethylformamide (DMF) (Kishida Chemical Co., Ltd.) in a tube for solid-phase synthesis (HiPep Laboratories, tube for solid-phase synthesis, LibraTube made of polypropylene, main body tube 5 mL, cap for solid-phase synthesis, Libra-Tube top cap made of polypropylene) overnight for swelling. Piperidine (Kishida Chemical Co., Ltd.)(20% in DMF, 2 mL) was added, and stirred by vortex for 1 minute, and thereafter the reaction solution was removed. Piperidine (20% in DMF, 2 mL) was added, and shaken at room temperature for 10 minutes, and thereafter the reaction solution was removed. Washing with DMF (2 mL) was performed five times, and the solvent was removed. It was confirmed that a small amount of the resin taken out gave a color with TNBS Test Kit (Tokyo Chemical Industry Co., Ltd.). Washing with each of methylene chloride (GODO Co., Ltd.) (2 mL) and DMF (2 mL) was performed three times, and the solvent was removed. A condensing agent cocktail (700 μL), and a mixed liquid (DIEA/NMP=2.75/14.25 (v/v), 700 μL) of N,N-diisopropylethylamine (DIEA) (NACALAI TESQUE, INC.) and N-methyl-2-pyrrolidone (NMP) (Kishida Chemical Co., Ltd.) were added to an N-terminal amino acid (0.30 mmol) for dissolution, and the solution was added to the resin. The condensing agent cocktail used was prepared by mixing 3.05 g of HBTU (Watanabe Chemical Industries, Ltd.), 1.25 g of HOBt-H$_2$O (Watanabe Chemical Industries, Ltd.), and 16 mL of DMF in advance. After shaking at room temperature for 15 minutes, the reaction solution was removed. Washing with DMF (2 mL) was performed five times, and the solvent was removed. It was confirmed that a small amount of the resin taken out did not give a color with TNBS Test Kit (Tokyo Chemical Industry Co., Ltd.). Washing with each of methylene chloride (2 mL) and DMF (2 mL) was performed three times, and the solvent was removed. Thereafter, the processes described above were repeated based on the amino acid sequence, and the peptide chain was elongated. The peptide chain was elongated by using Fmoc-Ala-OH H2O, Fmoc-Asp(OtBu)-OH, Fmoc-Arg(Pbf)-OH, Fmoc-Val-OH, Fmoc-Ile-OH, Fmoc-Met-OH, and Fmoc-Gly-OH (Watanabe Chemical Industries, Ltd.).

After the peptide elongation, the solvent was removed, acetic anhydride (KANTO CHEMICAL CO., INC.) (25% methylene chloride solution, 2 mL) was added, and shaken at room temperature for 5 minutes, and thereafter the reaction solution was removed. Washing with DMF (2 mL) was performed five times, and the solvent was removed. It was confirmed that a small amount of the resin taken out did not give a color with TNBS Test Kit. Washing with each of methylene chloride (2 mL) and DMF (2 mL) was performed three times, and the solvent was removed.

Next, a peptide was released from the resin according to the following procedure, and freeze-dried. A deprotection cocktail was added to the resin dried in a desiccator, slightly shaken at room temperature every 30 minutes, and left to stand for 90 minutes. The de-protection cocktail used was prepared by mixing 2375 μL of trifluoroacetic acid (TFA) (Kishida Chemical Co., Ltd.), 62.5 μL of triisopropylsilane (TIS) (Tokyo Chemical Industry Co., Ltd.), and 62.5 μL of water in advance. The filtrate was collected in a 15-mL centrifuge tube. TFA (500 μL) was added to a synthesis tube, and the filtrate was collected in the above centrifuge tube. These processes were repeated three times. Diethyl ether (Kishida Chemical Co., Ltd.) (40 mL) was added to the centrifuge tube where the filtrate was collected, and stirring was performed sufficiently. The supernatant was removed by centrifugation (4° C., 3500×g, 5 minutes). These processes were repeated three times. The sample was left to stand in a fume hood for 10 minutes and dried, and thereafter dried in a desiccator for 2 hours or more. The sample after drying was dispersed in ion-exchange water, and freeze-dried.

(2) Production of a Gel Comprising a Self-Assembling Peptide

A peptide powder after freeze-drying at 2.5 mg and 250 μL of D-MEM (containing 1×penicillin, 4.0 mM HEPES, 44 mM NaHCO$_3$; pH 7.4) were added to a 1-mL microtube (glass container having an inner diameter of 5 mm and a height of 5 cm; Maruemu Corporation, Model No. 1), and ultrasound was irradiated in a water bath type ultrasonic apparatus (AS12GTU, 35 kHz, 60 W), to thereby disperse the peptide at a concentration of 1.0% by weight. Thereafter, the microtube was left to stand in a CO$_2$ incubator (37° C., CO$_2$ concentration 5%) for 48 hours in a state standing vertically with the bottom surface thereof facing downward. Penicillin (Life Technologies Corporation, Model No. 15140148) was used as an antibacterial agent at 100 U/mL for the purpose of prevention of mold generation, and a $CO_2$ incubator was used for performing gelling in a condition similar to an in vivo condition.

(3) Fluidity Test

In order to test whether the peptide sample lost fluidity and gelled, the sample was sealed in a $CO_2$ incubator (37° C., $CO_2$ concentration 5%) and taken out of the incubator, the microtube was rapidly flipped vertically, and a photograph of the peptide sample was taken and recorded. In a case where a portion or all of the peptide sample remained on the bottom surface side of the microtube, the peptide sample was determined to have lost fluidity and gelled. On the other hand, in a case where all of the peptide sample dropped to the cap side of the microtube, the peptide sample was determined not to have gelled.

(Results)

Figure 2:
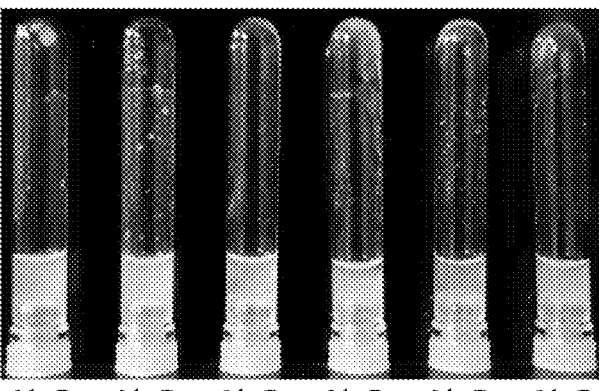
FIG. 2 shows the results of testing the gel formation ability of a peptide sample comprising valine as a hydrophobic amino acid.

FIGS. 1 and 2 show the results of the fluidity test for each peptide sample.

Among the eighteen types of peptides, twelve peptide samples: RIRARMDADIR (SEQ ID NO: 1), RIRADM-RADIR (SEQ ID NO: 2), RIRADMDARIR (SEQ ID NO: 3), RIDARMRADIR (SEQ ID NO: 4), RIDARMDARIR (SEQ ID NO: 5), RIDADMRARIR (SEQ ID NO: 6), RIRGDIRGDIR (SEQ ID NO: 7), RIRGDMRGDIR (SEQ ID NO: 8), RIRADIRADMR (SEQ ID NO: 9), RIDARM-RADMR (SEQ ID NO: 10), RMDARIDARIR (SEQ ID NO: 11), and RMDADMRARIR (SEQ ID NO: 12) were found to partially or entirely remain on the bottom surface side of the microtube after vertical flipping of the microtube, and were shown to have lost fluidity and gelled (FIG. 1).

On the other hand, in the cases of six types of peptides containing Val: RVRVRVDVDVR (SEQ ID NO: 13), RVRVDVRVDVR (SEQ ID NO: 14), RVRVDVDVRVR (SEQ ID NO: 15), RVDVRVRVDVR (SEQ ID NO: 16), RVDVRVDVRVR (SEQ ID NO: 17), and RVDVDVRVRVR (SEQ ID NO: 18), almost all of the sample dropped to the cap side of the microtube and did not gel in the same condition (FIG. 2).

The twelve types of peptides which showed gelling in FIG. 1 had Arg or Asp as a hydrophilic amino acid residue at the 1st, 3rd, 5th, 7th, 9th, and 11th positions from the N-terminal side, and Ile, Met, Ala, or Gly as a hydrophobic residue at the 2nd, 4th, 6th, 8th, and 10th positions from the N-terminal side. In contrast, the six types of peptides which did not gel in FIG. 2 were similar to said twelve types of peptides in having Arg or Asp as a hydrophilic amino acid residue at the 1st, 3rd, 5th, 7th, 9th, and 11th positions from the N-terminal side, but different therefrom in that they had Val as a hydrophobic residue at the 2nd, 4th, 6th, 8th, and 10th positions from the N-terminal side. The two cases of peptides were similar in that a hydrophobic amino acid and a hydrophilic amino acid were alternately linked by a peptide bond, and were expected to have very similar chemical properties. However, it was unexpectedly found that gelling is possible in physiological conditions only in a case where not Val, but Ile, Met, Ala, or Gly was placed as a hydrophobic residue at the 2nd, 4th, 6th, 8th, and 10th positions from the N-terminal side.

Example 2: Rheological Property of the Peptide Gel (Purpose)

Rheological property of a gel formed by a self-assembling peptide is analyzed.

(Method)

Among gels having a concentration of 1.0% by weight prepared in Example 1, gels formed by six types of peptide samples as examples: RIRARMDADIR peptide (SEQ ID NO: 1), RIRADMRADIR peptide (SEQ ID NO: 2), RIDARMRADIR peptide (SEQ ID NO: 4), RIDARM-DARIR peptide (SEQ ID NO: 5), RIDADMRARIR peptide (SEQ ID NO: 6), and RIRGDMRGDIR peptide (SEQ ID NO: 8) were subjected to measurement of the rheological property thereof.

The rheological property was measured for 250 μL of a sample with a rheometer (Malvern Panalytical, Kinexus lab+). Specifically, the sample was sandwiched at a gap of 0.2 mm between plates, and subjected to measurement at 20° C.

The storage elastic modulus G' and the loss elastic modulus G" of a gel formed by each peptide are obtained by measurement of the rheological property. The storage elastic modulus G' represents a component stored in an object, of the energy generated by an external force to the object and a strain, and the loss elastic modulus G" represents a component externally diffused. In a case where a measurement specimen is a gel, the storage elastic modulus G' generally exceeds the loss elastic modulus G".

(Results)

Figure 3:
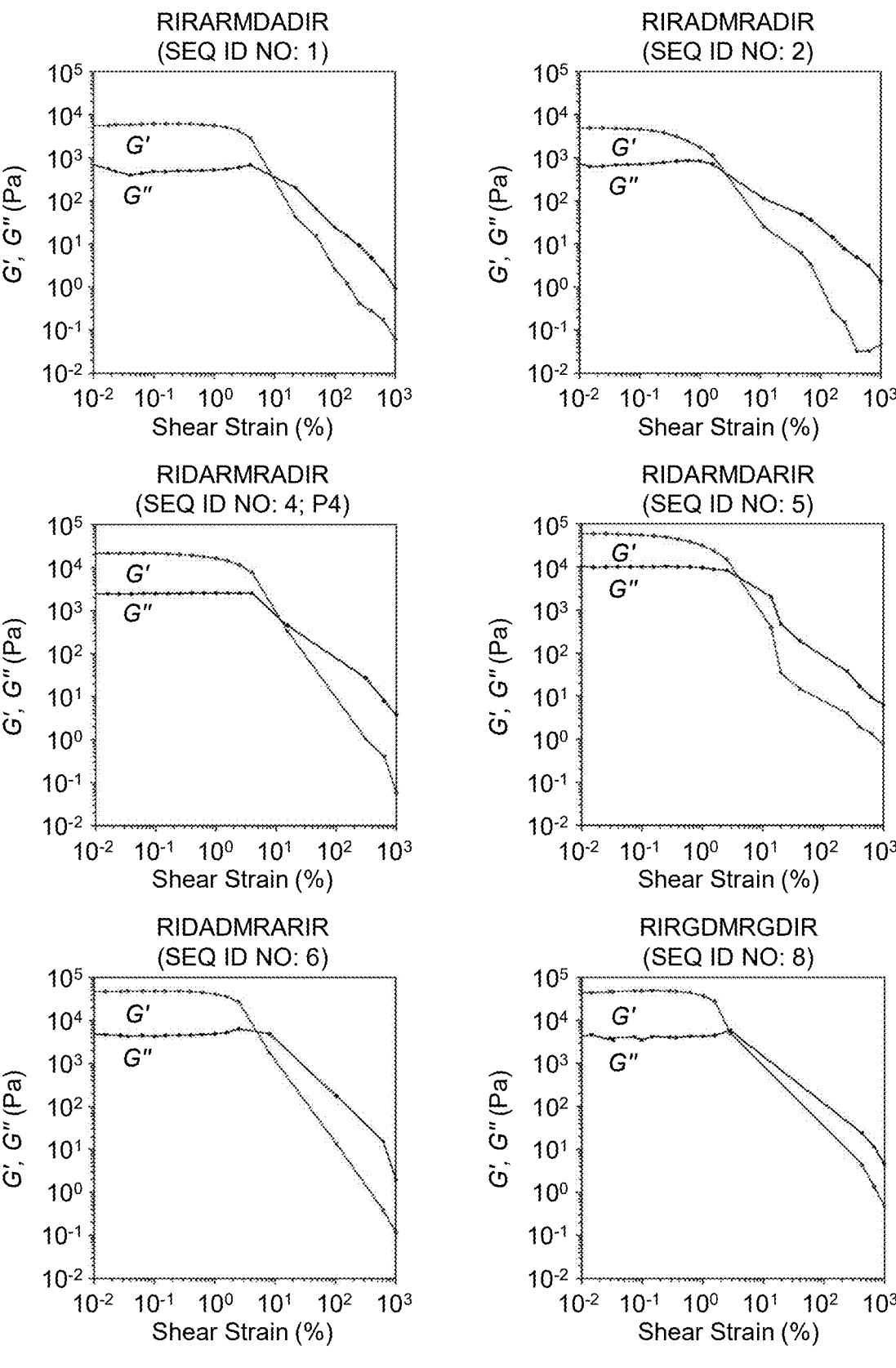
FIG. 3 shows the results of measuring rheological property. The horizontal axis represents the shear strain, and the vertical axis represents the storage elastic modulus G' and the loss elastic modulus G".

The measurement results of the rheological property of the six types of peptide samples are shown in FIG. 3.

The storage elastic modulus G' exceeded the loss elastic modulus G" in all the six types of peptide samples subjected to measurement. It was shown from the results that non-fluidic solid objects formed by the six types of peptide samples were gels.

Table 1 below shows the results of comparison between the storage elastic modulus G' measured with respect to each of the six types of peptide samples and the storage elastic modulus G' measured with respect to a known peptide gel.

TABLE 1

| Peptide | G' (Pa) | Solvent | Peptide concentration |
|---|---|---|---|
| RIDARMRADIR (SEQ ID NO: 4) | 21,300 | DMEM (pH 7.4) | 1.0% by weight |
| RIDARMDARIR (SEQ ID NO: 5) | 58,300 | DMEM (pH 7.4) | 1.0% by weight |
| RIRADMRADIR (SEQ ID NO: 2) | 4,830 | DMEM (pH 7.4) | 1.0% by weight |
| RIDADMRARIR (SEQ ID NO: 6) | 47,500 | DMEM (pH 7.4) | 1.0% by weight |
| RIRARMDADIR (SEQ ID NO: 1) | 6,500 | DMEM (pH 7.4) | 1.0% by weight |
| RIRGDMRGDIR (SEQ ID NO: 8) | 47,800 | DMEM (pH 7.4) | 1.0% by weight |
| (RADA)$_4$[*1] | 265 | 2.2% TFA aq. | 1.0% by weight |
| (RADA)$_4$[*1] | 30[*3] | pH 3-4 | 1.0% by weight |
| SPG178[*2] | 70[*3] | pH 7 | 1.0% by weight |
| SPG178[*2] | 300[*3] | pH 7 | 1.5% by weight |
| K$_2$(QFQL)$_3$K$_2$ | <500[*4] | 10 mM phosphate buffer or PBS (pH 7.4) | 2.0% by weight |

[*1]RADARADARADARADA (SEQ ID NO: 19)
[*2]RLDLRLALRLDLR (SEQ ID NO: 20)
[*3]Komatsu, S. et al. Plos One, 2014, 9 (7), e102778.
[*4]Bakota, E. L. et al. Biomacromolecules, 2013, 14 (5), 1370-1378.

As shown in Table 1, it was found that a gel formed by the peptide of the present invention has a dramatically high elastic modulus as compared with known gelling peptides such as $(RADA)_4$ (SEQ ID NO: 19), SPG178 (SEQ ID NO: 20), and $K_2(QFQL)_3K_2$ (SEQ ID NO: 51). In other words, the peptide of the present invention can form a dramatically hard gel as compared with the known peptide gelling agent.

For example, SPG178 (SEQ ID NO: 20) as a known peptide gelling agent in Table 1 forms a gel in a condition of pH 7.0 and a concentration of 1.0 or 1.5% by weight, but the storage elastic modulus G' of the gel is only 70 to 300 (Komatsu, S. et al. Plos One, 2014, 9 (7), e102778), and is less than the elastic modulus (about $10^3$) of mayonnaise or ketchup as in Table 2 shown below as reference.

TABLE 2

| Food | Elastic modulus (Pa) |
|---|---|
| Gum | $10^5$ |
| Boiled fish paste | $10^4$ |
| Konjak | |
| Coffee jelly | |
| Mayonnaise | $10^3$ |
| Ketchup | |
| Yogurt | $10^2$ |
| Yolk of egg | $10^1$ |

$K_2(QFQL)_3K_2$ (SEQ ID NO: 51) as another known peptide gelling agent shown in Table 1 forms a gel in PBS (pH 7.4) under a condition of a concentration of 2.0% by weight, but the storage elastic modulus G' of the gel is less than 500 (Bakota, E. L. et al. Biomacromolecules, 2013, 14 (5), 1370-1378) and is also less than the elastic modulus (about $10^3$) of mayonnaise or ketchup as shown in Table 2. Therefore, with a gel formed by $K_2(QFQL)_3K_2$, stable use is difficult when introduced in vivo.

On the other hand, the storage elastic modulus G' of a gel formed by the peptide of the present invention reached 4,000 to 60,000 (Table 1), and showed an elastic modulus comparable with or more than that (about $10^4$) of konjak or coffee jelly shown in Table 2.

It was shown from the above results that the peptide of the present invention has a dramatically excellent elastic modulus and an excellent durability as compared with known peptide gelling agents.

Furthermore, the peptide of the present invention has a short amino acid sequence as compared with known gelling peptides such as $(RADA)_4$ (SEQ ID NO: 19), SPG178 (SEQ ID NO: 20), and $K_2(QFQL)_3K_2$ (SEQ ID NO: 51), and thus is advantageous in that it can be chemically synthesized in a large amount at a low cost.

Example 3: Measurement of Circular Dichroism Spectrum (Purpose)

A circular dichroism spectrum is measured for the purpose of analyzing a steric structure of the self-assembling peptide.

The "circular dichroism" refers to a phenomenon in which a difference in absorbance occurs between left-handed circularly polarized light and right-handed circularly polarized light when a protein absorbs a circularly polarized light. In a case where a β-sheet structure is contained in the steric structure of a protein, a negative cotton effect around 220 nm is observed in a circular dichroism spectrum.

(Method)

Among the peptide gels having a concentration of 1.0% by weight prepared in Example 1, three types of peptides as examples: RIDARMRADIR peptide (SEQ ID NO: 4), RIRADMRADIR peptide (SEQ ID NO: 2), and RIDARMDARIR peptide (SEQ ID NO: 5) were subjected to measurement of circular dichroism spectra at 20° C., 40° C., 60° C., and 80° C. and circular dichroism spectra when re-cooled from 80° C. to 20° C.

The circular dichroism spectrum was measured with a JASCO J-1100 CD Spectrometer by using an assembly cell (GL Sciences, AB20-UV-0.1, cell length 0.1 mm). The measurement range was from 190 to 400 nm, the data-obtaining interval was 0.2 nm, the scanning speed was 200 nm/min, and the specimen concentration was 1.0% by weight. When the circular dichroism spectrum was measured, the temperature was controlled with JASCO temperature regulation unit and a water-cooled Peltier cell holder PTC-514.

(Results)

Figure 4:
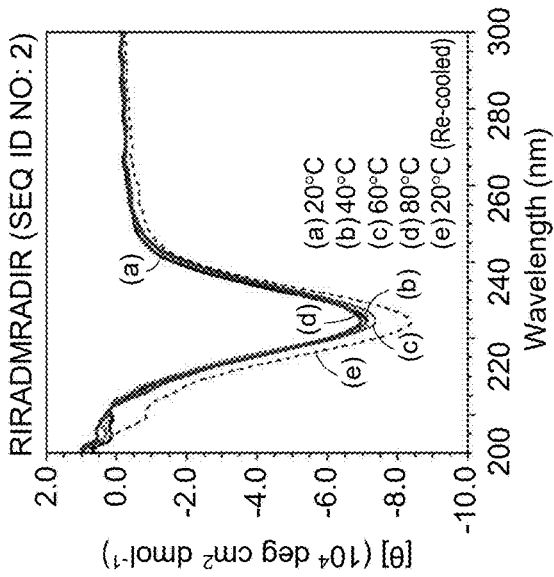
FIG. 4 shows the results of measuring circular dichroism spectra.
Figure 4:
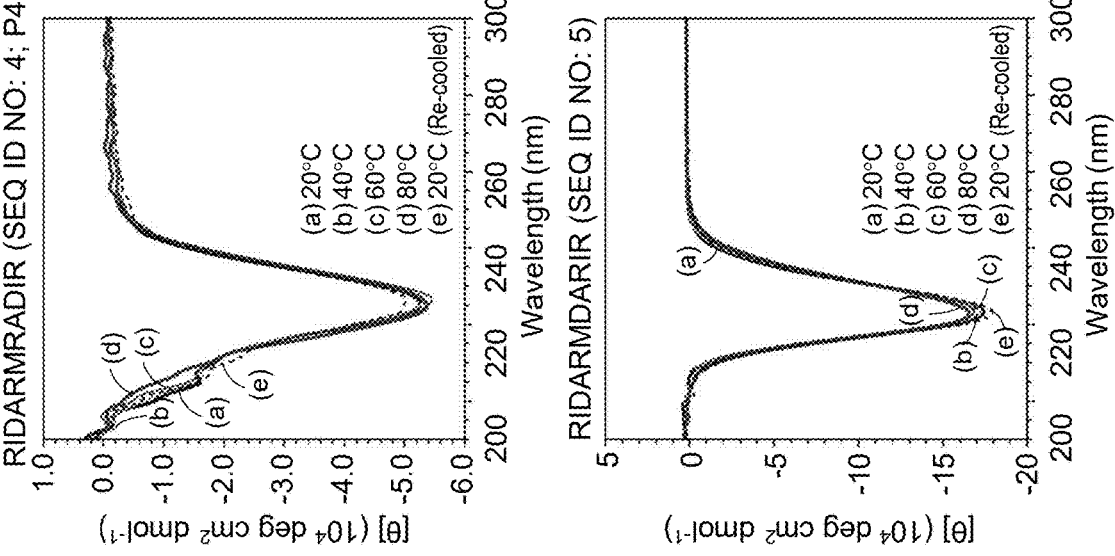

The measurement results of circular dichroism spectra are shown in FIG. 4.

All three types of peptide samples: RIDARMRADIR peptide (SEQ ID NO: 4), RIRADMRADIR peptide (SEQ ID NO: 2), and RIDARMDARIR peptide (SEQ ID NO: 5) showed the negative cotton effect around 220 nm. Since the effect is a characteristic signal assigned to the β-sheet structure, it was shown that the peptide forming the gel self-assembled into a β-sheet form.

The three types of peptide samples maintained the negative cotton effect around 220 nm in a condition of 20 to 80° C. Thus, it was shown that the β-sheet structure constituting the peptide gel was stably maintained in the temperature range from 20 to 80° C.

Example 4: Evaluation of Cell Adhesiveness (Purpose)

Cell adhesiveness of a peptide gel is evaluated.

(Method)

Among the peptide gels prepared in Example 1, three types of peptides as examples: RIRADMRADIR peptide (SEQ ID NO: 2), RIDARMRADIR peptide (SEQ ID NO: 4), and RIDARMDARIR peptide (SEQ ID NO: 5) were subjected to evaluation of cell adhesiveness.

A peptide sample having a concentration of 1.0% by weight was prepared by the same method as in Example 1. The peptide sample at 50 μL was dropped on a chamber slide (Merck Millipore, Millicell EZ 8-well glass) and dried under reduced pressure using a centrifugal concentrator (TAITEC CORPORATION, VC-96W), to thereby produce a chamber slide coated with the peptide. After $1.8 \times 10^5$ of mouse fetus-derived 3T3 cells (NIH3T3 cells) were suspended in 250 μL of a DMEM medium (containing 44 mM $NaHCO_3$, Gibco, 11995-065) containing 10% serum and seeded onto the chamber slide coated with the peptide, incubation was performed in a $CO_2$ incubator (37° C., $CO_2$ concentration 5%) for 30 minutes. The chamber slide was washed with PBS, and cells not adhering thereto were removed. The adhering cells remaining after the washing were immobilized with 4% PFA, and then subjected to DAPI staining. The number of adhering cells was measured according to stereology as a strict quantitative determination technique which eliminates sampling biases. Specifically, nine frames of 100 μm×100 μm were created in a region of 300 μm×300 μm, and the number of cells in each of the frames was counted. The resulting number of cells was converted into the number of cells in a region of 1 mm×1 mm. In the present Example, a (RADA)$_4$ peptide (SEQ ID NO: 19), which is known to form a cell-adhesive peptide gel, was used as a control.

(Results)

Figure 5:
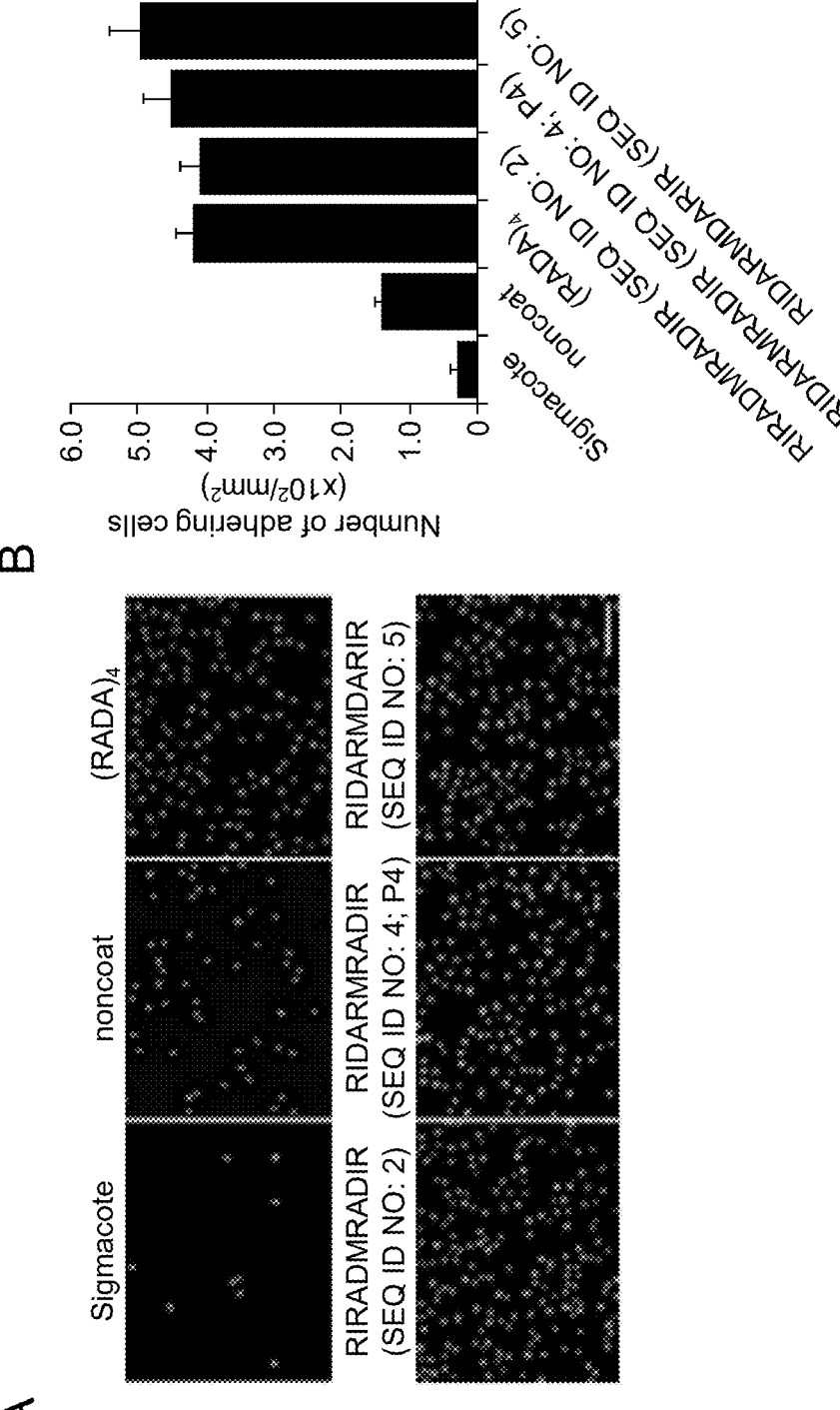
FIG. 5 shows the results of evaluating cell adhesiveness. DAPI staining of cells adhering to each peptide gel (A), and the number of adhering cells (B) are shown. Error bars represent standard deviation.

FIG. 5 shows DAPI staining of adhering cells and the number of adhering cells.

In the case of siliconizing treatment of a chamber slide surface by Sigmacote (Sigma-Aldrich Co. LLC, SL2-25ML) (FIG. 5, "Sigmacote") and in the case of no treatment of a chamber slide surface where active adhesion is not promoted (FIG. 5, "noncoat"), the number of cells adhering to the chamber slide is small. In contrast, RIRADMRADIR peptide (SEQ ID NO: 2), RIDARMRADIR peptide (SEQ ID NO: 4), and RIDARMDARIR peptide (SEQ ID NO: 5) according to the present invention were shown to have cell adhesiveness comparable with or more than a (RADA)$_4$ peptide (SEQ ID NO: 19).

It has been shown from the results that the peptide gelling agent of the present invention can be used as an artificial extracellular matrix or a cell scaffold material having cell adhesiveness.

Example 5: Incorporation of the GFP-P4 Fusion Peptide into a Peptide Gel (Purpose)

The efficiency of incorporation of a fusion peptide formed by linking a GFP protein and a self-assembling peptide into a peptide gel is evaluated. Although a peptide consisting of an amino acid sequence RIDARMRADIR (SEQ ID NO: 4) (hereinafter, referred to as "P4 peptide") was used as one example of the self-assembling peptide of the present invention in Examples below, it is clear that the effect obtained with the P4 peptide can be also obtained similarly with all of the other self-assembling peptides according to the present invention.

(Method)

(1) Preparation of P4 Peptide Solution

A P4 peptide solution comprising the P4 peptide consisting of an amino acid sequence represented by SEQ ID NO: 4 at a concentration of 1.0% by weight was prepared by the same method as in Example 1.

(2) Preparation of GFP-P4 Fusion Peptide

A plasmid expressing a GFP-P4 fusion peptide formed by fusing a peptide consisting of an amino acid sequence RIDARMRADIR (SEQ ID NO: 4) (P4 peptide) to the C-terminal side of a GFP protein, and a plasmid expressing a GFP protein to which P4 peptide is not fused were produced by the following method.

A sequence portion encoding GFP and 6×HisTag was subjected to PCR amplification with a CAG-Fw1 primer (SEQ ID NO: 23) and a P4-Rv1 primer (SEQ ID NO: 24), using as a template a pCAG-GFP-RADA16 plasmid described in Japanese Patent Application No. 2020-45109. Next, the amplification product was used as a template for PCR amplification with a CAG-Fw2 primer (SEQ ID NO: 25) and a P4-Rv2 primer (SEQ ID NO: 26), producing a GFP-P4 fragment. The GFP-P4 fragment was excised by NheI/XhoI, and then inserted into pCAG-CST, and a pCAG-GFP-P4 plasmid for expression of a GFP-P4 fusion peptide was produced.

Next, a GFP-P4 fusion peptide and a GFP protein were expressed and extracted by the method described in the previous literatures by the present inventors (Oshikawa, M. et al., Adv Healthc Mater. 2017; 6(11):10.1002/adhm.201700183, PMID: 28488337). Specifically, a pCAG- GFP-P4 and a pCAG-GFP plasmid were transfected to 293T cells. After culturing for 4 days, cells were lysed by 500 µL of a liquid for cell lysis (0.5% Nonidet P-40, 120 mM NaCl, 50 mM Tris-HCl (pH8.0)). For the lysate fraction, replacement with a 0.1×PBS (137 mM NaCl, 2.70 mM KCl, 0.810 mM Na$_2$HPO$_4$, 0.147 mM KH$_2$PO$_4$ (pH7.4)) solution and concentration were carried out using an ultrafiltration column (Merck KGaA, amicon ultra 10K). A GFP-RADA16 fusion peptide used as a control was prepared by the method disclosed in Japanese Patent Application No. 2020-45109.

The concentrations of the resulting GFP-P4 fusion peptide, GFP-RADA16 fusion peptide, and GFP protein were measured by a sandwich ELISA method. An anti-GFP chicken antibody (Abcam, ab13970) was used as a capture antibody, and an anti-GFP rabbit antibody (Abcam, ab290) was used as a detection antibody.

(3) Measurement of GFP Incorporation Rate

In a 1.5-mL tube, 40 µL of a GFP-P4 fusion peptide solution, a GFP-RADA16 fusion peptide solution, or a GFP solution diluted with H$_2$O so that the molar ratio would become 1/10$^5$ (referred to as "Amount of addition" of GFP fusion peptide or GFP), and furthermore 10 µL of a 10×DMEM solution (Thermo Fisher Scientific, 12100061) to which a 100 mM HEPES solution had been added were added to 50 µL of a 2% P4 peptide solution or a 1% RADA16 peptide solution, and gelling was carried out by pipetting. Thereafter, washing with 500 µL of a PBS solution (137 mM NaCl, 2.70 mM KCl, 8.10 mM Na$_2$HPO$_4$, 1.47 mM KH$_2$PO$_4$ (pH7.4)) was performed three times. The GFP fusion peptide or GFP concentration in the supernatant was measured by a sandwich ELISA method, and the measurement was assigned as a non-incorporated fraction (referred to as "Non-incorporated amount" of GFP fusion peptide or GFP). The "Incorporated amount" of GFP fusion peptide or GFP was calculated as [Amount of addition−Non-incorporated amount], and Incorporation rate (%)=Incorporated amount/Amount of addition was determined.

(Results)

Figure 6:
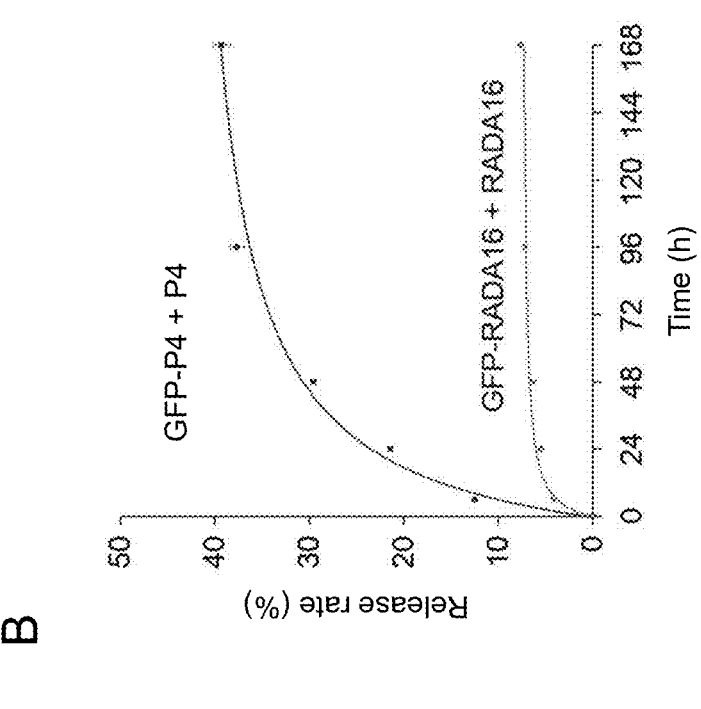
FIG. 6A shows the results of measuring the incorporation rate of the GFP-P4 fusion peptide to the P4 peptide gel, the incorporation rate of the GFP protein to the P4 peptide gel, the incorporation rate of the GFP-RADA16 fusion peptide to the RADA16 peptide gel, and the incorporation rate of the GFP protein to the RADA16 peptide gel.
FIG. 6B shows the results of measuring the release rate of the GFP-P4 fusion peptide from the P4 peptide gel and the release rate of the GFP-RADA16 fusion peptide from the RADA16 peptide gel. The figure shows the average value of three measurement results, and error bars represent the standard deviation.
Figure 6:
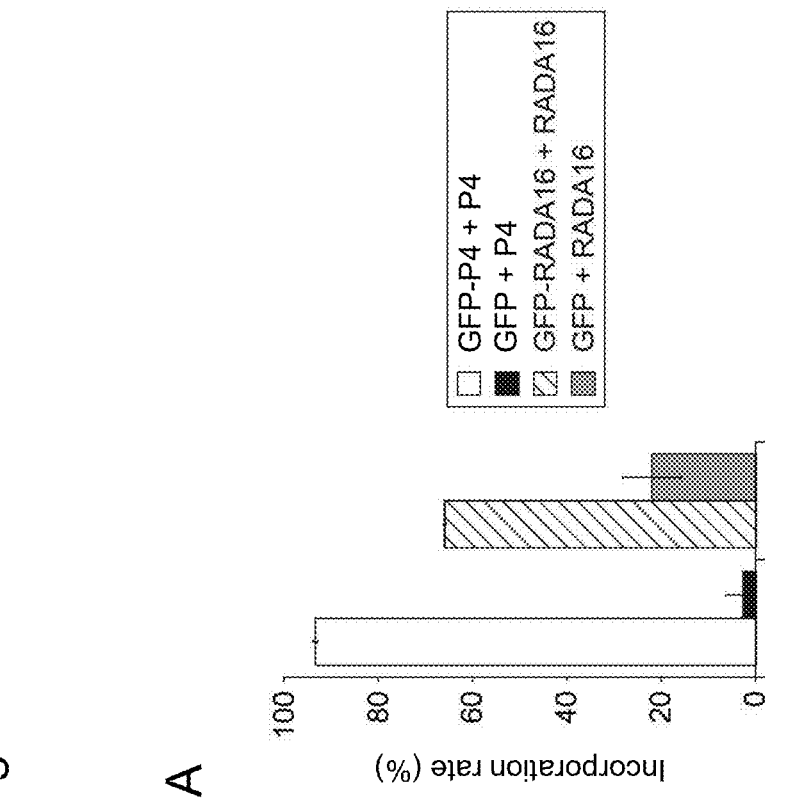

FIG. 6A shows the results of measuring the incorporation rate of the GFP-P4 fusion peptide to the P4 peptide gel, the incorporation rate of the GFP protein to the P4 peptide gel, the incorporation rate of the GFP-RADA16 fusion peptide to the RADA16 peptide gel, and the incorporation rate of the GFP protein to the RADA16 peptide gel.

The GFP protein to which P4 peptide is not fused was mostly not incorporated into the P4 peptide gel (FIG. 6A, "GFP+P4"). In contrast, the GFP-P4 fusion peptide was incorporated into the P4 peptide gel at an extremely high efficiency of more than 90% (FIG. 6A, "GFP-P4+P4"). On the other hand, the GFP-RADA16 fusion peptide was efficiently incorporated into the RADA16 peptide gel, but the incorporation efficiency was less than 70% (FIG. 6A, "GFP-RADA16+RADA16").

It was shown from the above results that the incorporation rate to the P4 peptide gel was greatly increased by fusing a P4 peptide to GFP. It was also shown that a P4 peptide considerably increased the incorporation rate as compared with a RADA16 peptide.

Example 6: Sustained Release of GFP-P4 Fusion Peptide from Peptide Gel (Purpose)

The release rate of a GFP-P4 fusion peptide from a P4 peptide gel is measured and the property of sustained-release is evaluated.

(Method)

The release rate was measured by the following method. The P4 peptide gel into which the GFP-P4 fusion peptide was incorporated, or the RADA16 peptide gel into which the GFP-RADA16 fusion peptide was incorporated, in Example 5, was suspended in 200 μL of a PBS solution comprising 10% FBS, and continuously stirred with a high speed shaker (TOKYO RIKAKIKAI CO., LTD., CM-1000) in conditions of 37° C. and 500 rpm. The concentration of the GFP fusion peptide or GFP comprised in the supernatant of a sample was measured at each time point after 0, 6, 12, 24, 72, 96, and 168 hours by a sandwich ELISA method, the amount of the GFP fusion peptide or GFP released into the supernatant (referred to as "Released amount") was determined, and Release rate (%)=Released amount/Incorporated amount was determined.

(Results)

FIG. 6B shows the results of measuring the release rate of the GFP-P4 fusion peptide from the P4 peptide gel and the release rate of the GFP-RADA16 fusion peptide from the RADA16 peptide gel. Almost no release of the GFP-RADA16 fusion peptide from the RADA16 peptide gel was observed on or after 6 hours, and the release rate after 168 hours was merely about 5% (FIG. 6B, "GFP-RADA16+RADA16"). In contrast, release of the GFP-P4 fusion peptide from the P4 peptide gel was sustained over a long period of time, and the release rate after 168 hours reached nearly to 40%.

It was shown from the results that the P4 peptide could allow for release of more functional molecule over a longer time as compared with the RADA16 peptide. Accordingly, it was shown that the P4 peptide gel had an excellent effect of sustained release.

Example 7: Incorporation of VEGF-P4 Fusion Peptide into Peptide Gel (Purpose)

The efficiency of incorporation of a VEGF-P4 fusion peptide formed by linking a VEGF peptide and a P4 peptide into a P4 peptide gel.

(Method)

A plasmid expressing a VEGF-P4 fusion peptide formed by fusing a peptide (P4 peptide) consisting of an amino acid sequence RIDARMRADIR (SEQ ID NO: 4), to the C-terminal side of a VEGF peptide, and a plasmid expressing a VEGF peptide to which P4 peptide is not fused were produced by the following method.

A sequence portion encoding VEGF and 6×HisTag was subjected to PCR amplification with a CAG-Fw1 primer (SEQ ID NO: 23) and a P4-Rv1 primer (SEQ ID NO: 24) using as a template a pCAG-VEGF-A16G plasmid described in Japanese Patent Application No. 2020-45109. Next, the amplification product was used as a template for PCR amplification with a CAG-Fw2 primer (SEQ ID NO: 25) and a P4-Rv2 primer (SEQ ID NO: 26), producing VEGF-P4 fragment. The VEGF-P4 fragment was cut with NheI/XhoI, and then inserted into pCAG-CST, and thus a pCAG-VEGF-P4 plasmid for expression of a VEGF-P4 fusion peptide was produced.

Next, a VEGF-P4 fusion peptide and a VEGF peptide were expressed and extracted by the method described in previous literatures by the present inventors (Oshikawa, M. et al., Adv Healthc Mater. 2017; 6(11):10.1002/adhm.201700183, PMID: 28488337). Specifically, a pCAG-VEGF-P4 and a pCAG-VEGF plasmid were transfected to 293T cells, and culturing was performed for 7 days, thereby providing a culture supernatant. For this fraction, replacing with a 0.1×PBS (137 mM NaCl, 2.70 mM KCl, 0.810 mM $Na_2HPO_4$, 0.147 mM $KH_2PO_4$ (pH7.4)) solution and concentration were carried out with an ultrafiltration column (Merck KGaA, amicon ultra 10K).

The concentrations of the resulting VEGF-P4 fusion peptide and VEGF peptide were measured by a sandwich ELISA method. An anti-VEGF goat antibody (R&D Systems, Inc., AF-493-NA) was used as a capture antibody, and a biotinylated anti-VEGF goat antibody (R&D Systems, Inc., R&D BAF493) was used as a detection antibody.

The efficiency of incorporation into the peptide gel was measured by the same method as in Example 5, and the incorporation rate (%) was determined.

(Results)

Figure 7:
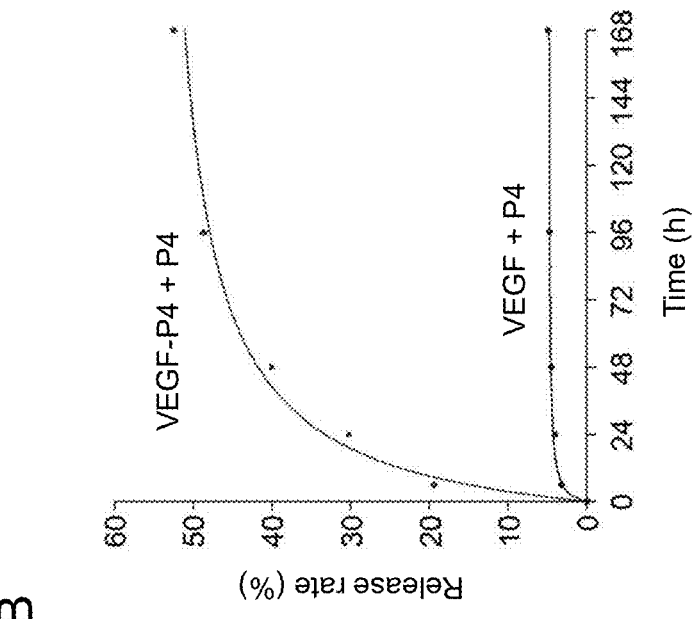
FIG. 7A shows the results of measuring the incorporation rate of the VEGF-P4 fusion peptide to the P4 peptide gel and the incorporation rate of the VEGF peptide to the P4 peptide gel.
FIG. 7B shows the results of measuring the release rate of the VEGF-P4 fusion peptide from the P4 peptide gel and the release rate of the VEGF peptide from the P4 peptide gel. The figure shows the average value of three measurement results, and error bars represent the standard deviation.
Figure 7:
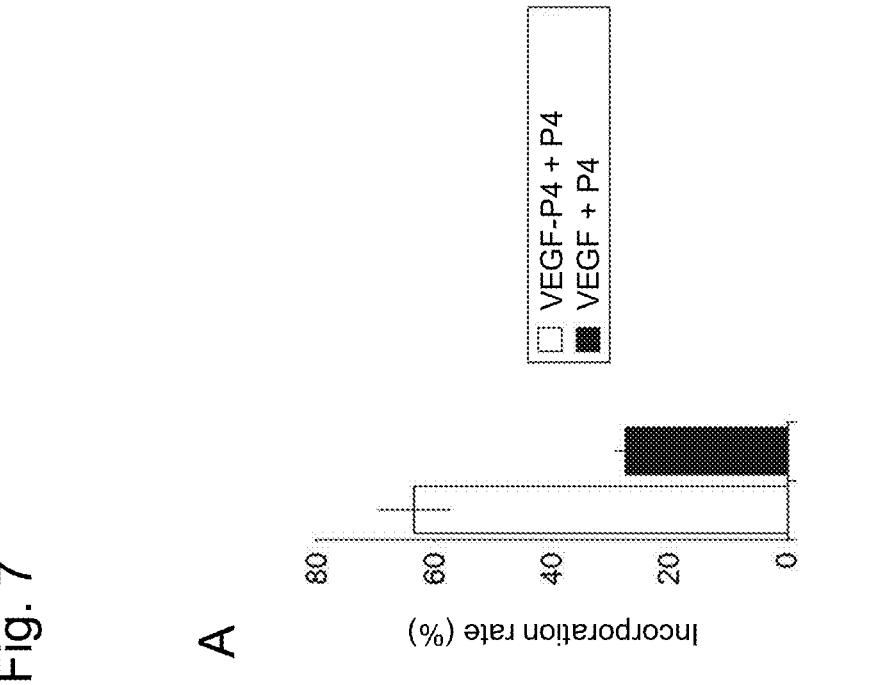

FIG. 7A shows the results of measuring the incorporation rate of the VEGF-P4 fusion peptide to the P4 peptide gel and the incorporation rate of the VEGF peptide to the P4 peptide gel.

The VEGF-P4 fusion peptide exhibited a high incorporation rate into the P4 peptide gel, as compared with the VEGF peptide to which P4 peptide is not fused. It was shown from the results that incorporation into the P4 peptide gel was greatly promoted by fusing the P4 peptide to the VEGF peptide.

Example 8: Sustained Release of VEGF-P4 Fusion Peptide from P4 Peptide Gel (Purpose)

The release rate of a VEGF-P4 fusion peptide from a P4 peptide gel is measured and the property of sustained-release is evaluated.

(Method)

The concentration of the VEGF-P4 fusion peptide or VEGF peptide comprised in the supernatant of a sample was measured at each time point after 0, 6, 12, 24, 72, 96, and 168 hours by a sandwich ELISA method. The proportion of released amount (release rate (%))=Released amount/Incorporated amount at each time point relative to the amount of the VEGF-P4 fusion peptide or VEGF peptide which had been incorporated into the P4 peptide gel was determined.

(Results)

FIG. 7B shows the results of measuring the release rate of the VEGF-P4 fusion peptide and the VEGF peptide from the P4 peptide gel. Almost no release of the VEGF peptide from the P4 peptide gel was observed (FIG. 7B, "VEGF+P4"). In contrast, release of the VEGF-P4 fusion peptide from the P4 peptide gel was sustained over a long period of time, and the release rate after 168 hours reached about 50%.

It was shown from the results that excellent properties of sustained-release can be obtained by incorporating the VEGF-P4 fusion peptide into the P4 peptide gel.

Example 9: Effect of Improving Walking Function in Mouse Brain Infarction Model by P4 Peptide Gel Containing VEGF-P4 Fusion Peptide (Purpose)

A P4 peptide gel incorporating a VEGF-P4 fusion peptide is embedded into the brain of a mouse brain infarction model, and the treatment effect on walking disability is evaluated.

(Method)

A peptide gel was produced in a 1.5-ml tube by adding 25 μL of a VEGF-P4 fusion peptide or a VEGF peptide diluted with $H_2O$ so that the molar ratio would become $1/10^5$, to 25

µL of a 2% P4 peptide solution. After pipetting, the sample was left to stand in a $CO_2$ incubator for 3 days, and a gel was formed.

Figure 8:
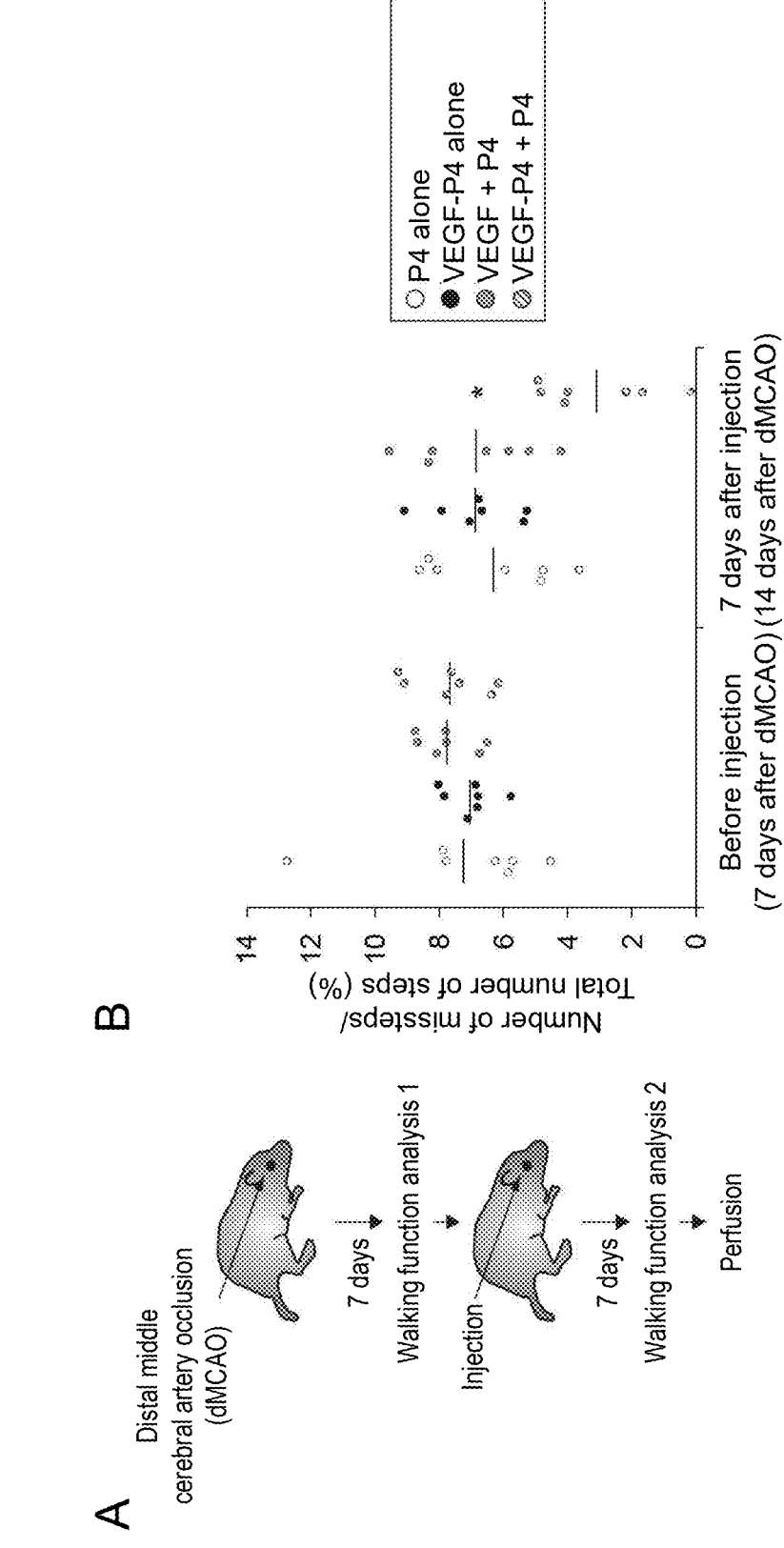
FIG. 8 shows the effect of improving walking function by the VEGF-P4 fusion peptide in a mouse brain infarction model.

A mouse brain infarction model used was a distal middle cerebral artery occlusion (dMCAO) model reported by the present inventors (Oshikawa, M. et al., Adv Healthc Mater. 2017; 6(11):10.1002/adhm.201700183, PMID: 28488337). The first walking function analysis was performed (FIG. 8A, "Walking function analysis 1") on day 7 after production of the brain infarction model, according to the method described in the previous literatures by the present inventors (Jinnou, H., et al., Cell Stem Cell, 2018, 22(1), 128-137.e9., PMID: 29276142). After the first walking function analysis, the peptide gel was administered from the distal middle cerebral artery in the temporal part of the head during craniotomy when the dMCAO model was produced (FIG. 8A, "Injection"). The dose was 2 µL per individual. The walking function analysis was performed (FIG. 8A, "Walking function analysis 2") on day 7 after administration (day 14 after production of the brain infarction model), and thereafter perfusion and fixation were performed and brain sections were prepared. The walking function was evaluated by calculating the proportion of the number of slipped steps in the total number of steps (Number of missteps/Total number of steps (%)).
(Results)

FIG. 8B shows the results of administration of the peptide gel to the mouse brain infarction model. No improvement in walking function was observed in the cases of administration of a VEGF peptide-free P4 peptide gel alone ("P4 alone"), a VEGF-P4 fusion peptide alone ("VEGF-P4 alone"), and a P4 peptide gel comprising a VEGF peptide to which P4 peptide is not fused ("VEGF+P4 alone"). In contrast, the proportion of the number of slipped steps in the total number of steps was reduced and the improvement effect of the walking function was observed in the case of administration of a P4 peptide gel comprising a VEGF-P4 fusion peptide ("VEGF-P4+P4 alone").

Accordingly, it was shown that restoration of the impaired walking function caused by brain infarction was promoted by administration of the VEGF-P4 fusion peptide contained in the P4 peptide gel. It was shown from the results and the results in the following Examples that sustained release of the VEGF-P4 fusion peptide from the P4 peptide gel enabled supplying the VEGF function over a long period of time and allowed for sustained promotion of vascularization (Example 11), suppression of neurodegeneration (Example 12), and suppression of reduction of the number of neuronal cells (Example 13), thereby allowing for rapid recovery of the brain function from brain infarction.

Example 10: Effect on Volumes of Damage Core and Penumbra Region (Purpose)
The presence or absence of difference in the volume of damage core and penumbra region between individual conditions in Example 9 is examined.
(Method)
A brain section of the distal middle cerebral artery to which the peptide gel was administered in Example 9 was produced. The section was subjected to visualization of activated microglia by DyLight 488-labelled tomato lectin (LEL) (Vector Laboratories, Inc., DL-1174) staining, staining with a neuron marker anti-NeuN antibody (Merck Millipore, MAB377), and nuclear staining with DAPI (Sigma-Aldrich Co. LLC, D9542) at the same time. A LEL-positive region showing the activated microglia was defined as the damage core (core), and a LEL-negative and NeuN-weakly positive region was defined as the penumbra region. The respective volumes of the damage core and the penumbra region were measured according to stereology (Micro-BrightField Japan, Inc., Stereo investigator).
(Results)

Figure 9:
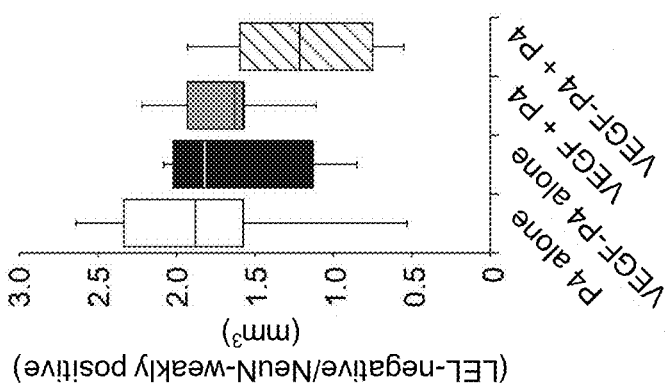
FIG. 9 shows the results of (A) tomato lectin (LEL)/DAPI staining, (B) LEL staining, (C) NeuN staining, and (D) LEL/NeuN staining of a brain section of the distal middle cerebral artery of a mouse brain infarction model to which the P4 peptide gel comprising the VEGF-P4 fusion peptide was administered. The positions of (B) to (D) are shown in the frame in (A). The arrow in (A) indicates a LEL-positive region (damage core).
Figure 9:
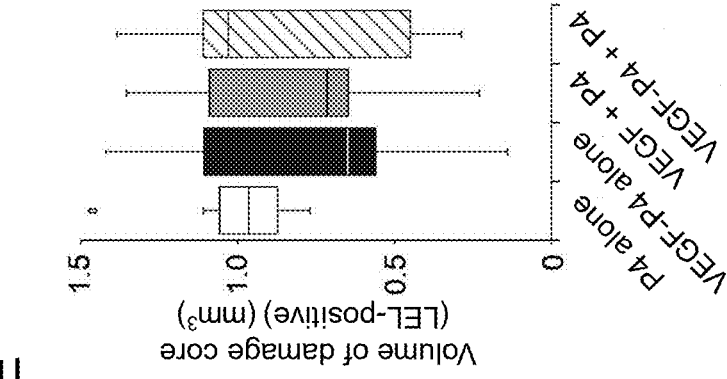
Figure 9:
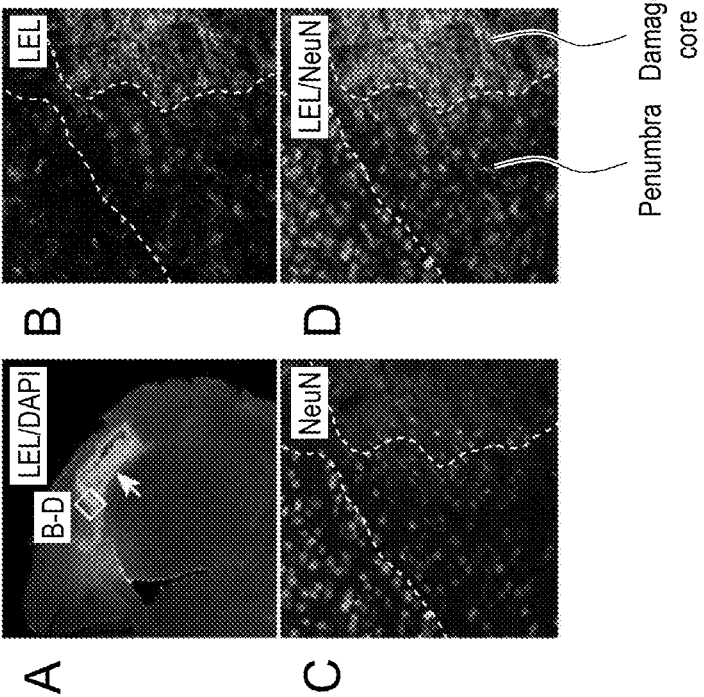

No significant changes in volumes of the damage core and the penumbra region were observed in all the cases of administration of the VEGF peptide-free P4 peptide gel alone, and the VEGF-P4 fusion peptide alone, the VEGF peptide to which P4 peptide is not fused, and the P4 peptide gel containing the VEGF-P4 fusion peptide (FIG. 9). Changes of the number of cells in each cell type were examined in the following Examples 11 to 13 based on the results.

Example 11: Effect of Promoting Vascularization (Purpose)
The presence or absence of the effect of promoting vascularization in each condition in Example 9 is examined.
(Method)
EdU was administered for one week every 8 hours after administration of the peptide gel in each condition in Example 9, and a brain section was produced after perfusion and fixation. EdU was administered according to the method described in the previous literature by the present inventors (Oshikawa, M., et al., Development, 2017, 144(18), 3303-3314). Cells positive for laminin as a marker for vascular endothelial cells were visualized by an anti-laminin antibody (Abcam, ab11575), and EdU was visualized by click reaction using Alexa 647 Azide (Invitrogen, A10277). The number of laminin-positive cells and the number of EdU/laminin-co-positive cells in the penumbra region were measured according to stereology.
(Results)

Figure 10:
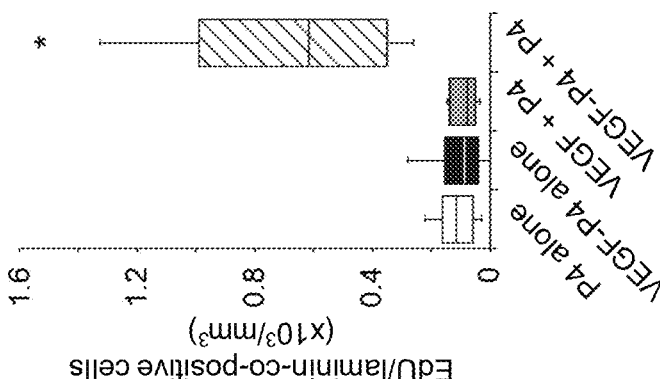
FIG. 10 shows the effect of promoting vascularization by the P4 peptide gel comprising the VEGF-P4 fusion peptide. The figure shows (A) laminin staining, (B) EdU staining, (C) DAPI staining, and (D) merge of a brain section of the distal middle cerebral artery of a mouse brain infarction model to which the P4 peptide gel comprising the VEGF-P4 fusion peptide was administered. The arrow indicates the position of an EdU-positive proliferating cell.
Figure 10:
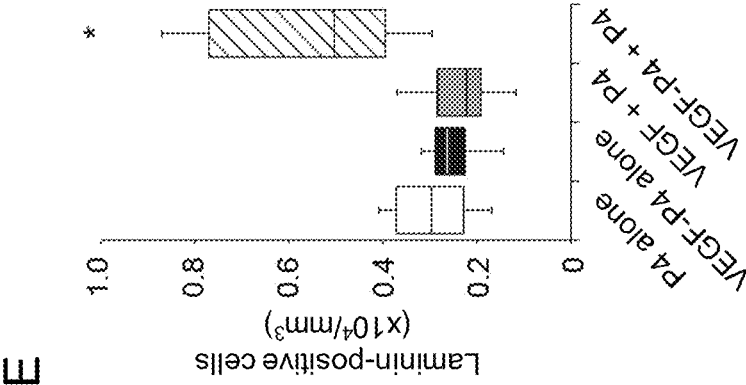
Figure 10:
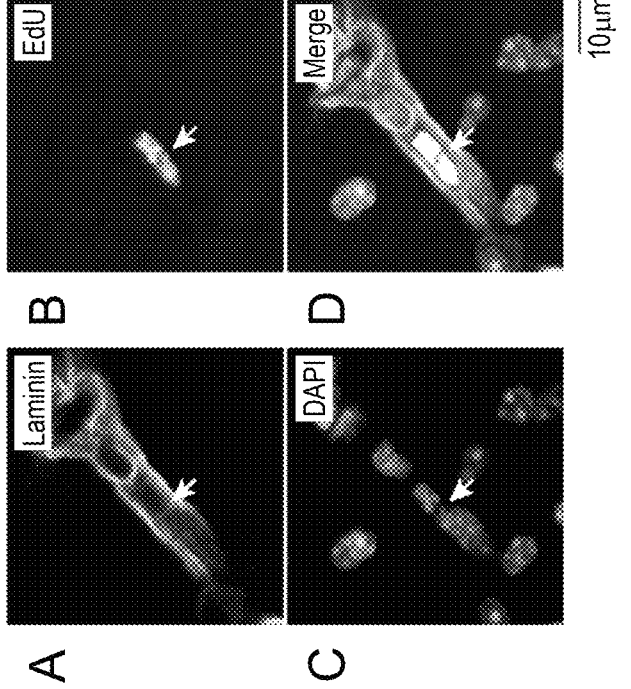

It was observed that the number of laminin-positive cells and the number of EdU/laminin-co-positive cells were significantly increased in the case of administration of the P4 peptide gel containing the VEGF-P4 fusion peptide, as compared with the cases of administration of the VEGF peptide-free P4 peptide gel alone, the VEGF-P4 fusion peptide alone, and the VEGF peptide to which P4 peptide is not fused (FIG. 10).

It was shown from the results that sustained release of the VEGF-P4 fusion peptide from the P4 peptide gel enables sustained supply of the VEGF function over a long period of time and promotes vascularization in the penumbra region after brain infarction.

Figure 11:
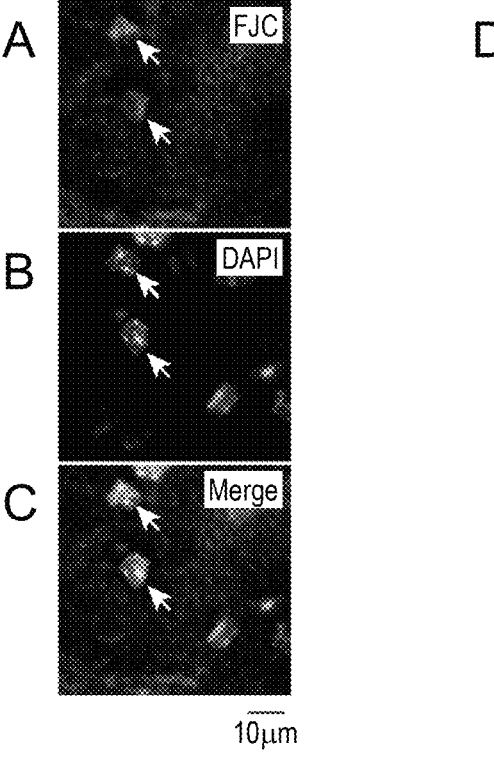
FIG. 11 shows the effect of suppressing neurodegeneration by the P4 peptide gel comprising the VEGF-P4 fusion peptide. The figure shows (A) FJC staining, (B) DAPI staining, and (C) merge in a penumbra region of a mouse brain infarction model. Arrows indicate the position of an FJC-positive degenerated neuron.

Example 12: Effect of Suppressing Neurodegeneration (Purpose)
The presence or absence of the effect of suppressing neurodegeneration in each condition in Example 9 is examined.
(Method)
After tissue staining was performed with Fluoro-Jade C (FJC) (Biosensis Pty. Ltd., TR-100-FJT) comprising a fluorescent dye that specifically binds to degenerating neurons, and DAPI, the number of FJC-positive cells in the penumbra region was measured according to stereology.
(Results)
A decrease in the number of FJC-positive cells was observed in the case of administration of the P4 peptide gel containing the VEGF-P4 fusion peptide (FIG. 11). It was shown from the results that sustained release of the VEGF-P4 fusion peptide from the P4 peptide gel resulted in suppression of neurodegeneration in the penumbra region after brain infarction.

Example 13: Effect of Suppressing Reduction of the Number of Neuronal Cells (Purpose)

The presence or absence of the effect of suppressing the reduction of the number of neuronal cells in each condition in Example 9 is examined.

(Method)

Immunological tissue staining was performed with an anti-NeuN antibody as a neuron marker, and nuclear staining was performed with DAPI (Sigma-Aldrich Co. LLC, D9542). The number of NeuN-positive cells in the penumbra region was measured according to stereology.

(Results)

Figure 12:
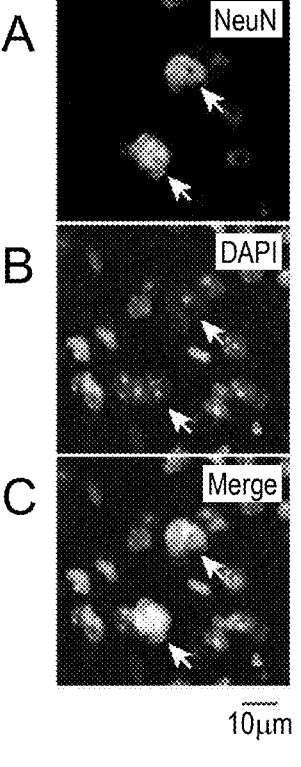
FIG. 12 shows the effect of suppressing the reduction of number of neuronal cells by the P4 peptide gel comprising the VEGF-P4 fusion peptide. The figure shows (A) NeuN staining, (B) DAPI staining, and (C) merge in a penumbra region of a mouse brain infarction model. Arrows indicate the position of a NeuN-positive neuron.
Figure 12:
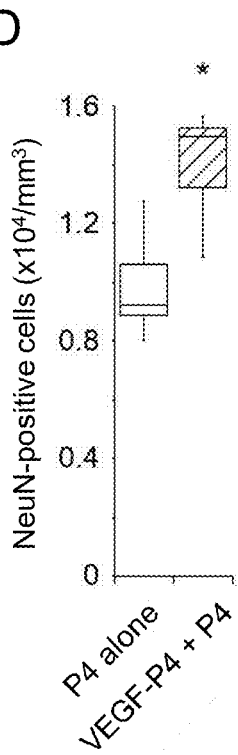

A significant increase in the number of NeuN-positive cells was observed in the case of administration of the P4 peptide gel containing the VEGF-P4 fusion peptide (FIG. 12). It was shown from the results that sustained release of the VEGF-P4 fusion peptide from the P4 peptide gel resulted in suppression of the reduction of the number of neuronal cells in the penumbra region after brain infarction.

Example 14: Sustained Release of K(FAM)-G-P4 Fusion Peptide from P4 Peptide Gel (Purpose)

The release rate of a FAM-P4 fusion peptide formed by linking fluorescein (FAM) and a self-assembling peptide from a P4 peptide gel is measured.

(Method)

(1) Incorporation of FAM-P4 Fusion Peptide into P4 Peptide Gel

Figure 13:
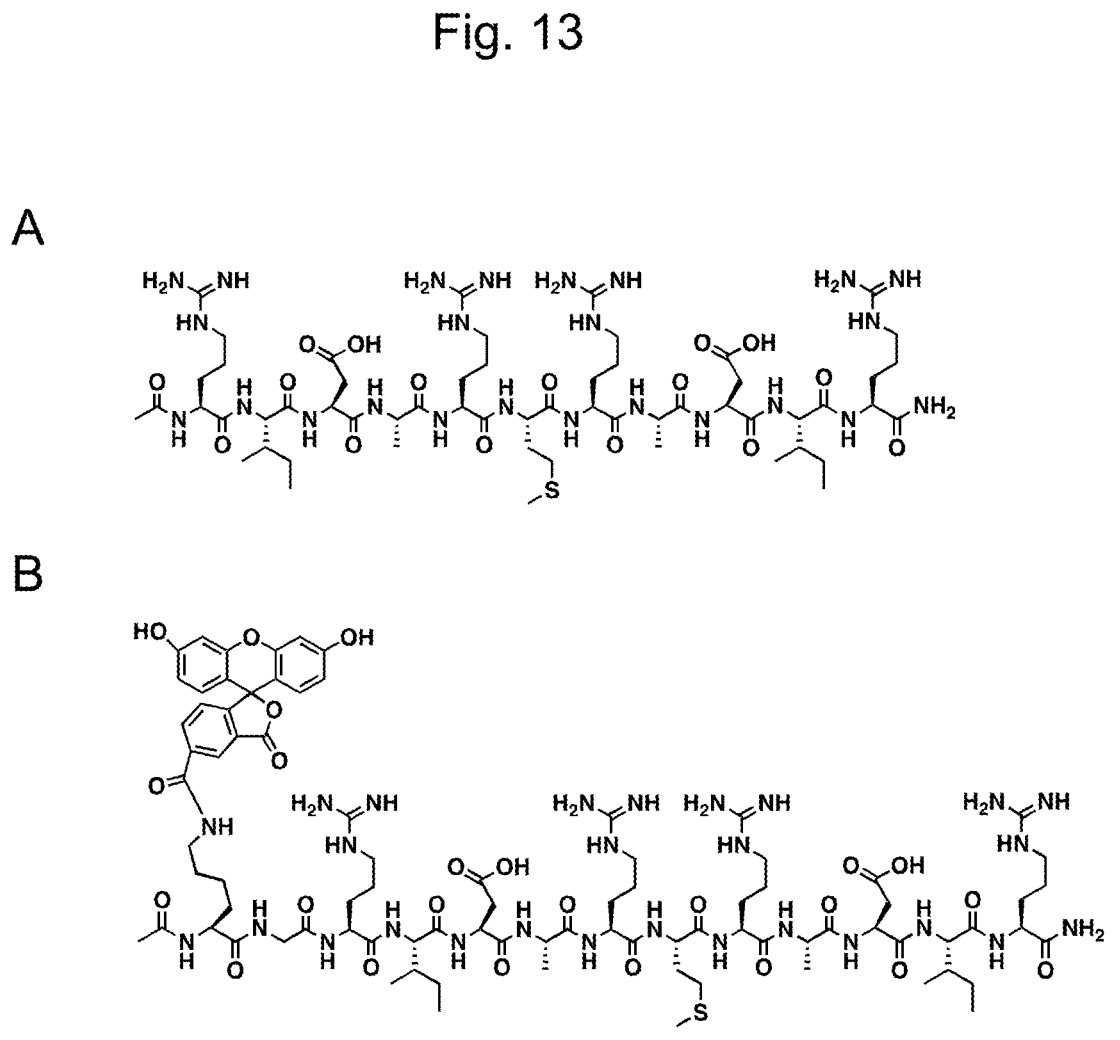

A K(FAM)-G-P4 fusion peptide formed by linking a peptide (P4 peptide, FIG. 13A) consisting of an amino acid sequence RIDARMRADIR (SEQ ID NO: 4), and fluorescein, was synthesized (FIG. 13B). Specifically, 5(6)-Carboxyfluorescein and a KG-P4-resin were bound by a solid-phase synthesis reaction, and a K(FAM)-G-P4 fusion peptide was synthesized by cutting out from a resin with TFA. A K(FAM)-G-P4 fusion peptide at a molar ratio of 1/100,000 and a DMEM+HEPES solution were added to a P4 peptide solution having a concentration of 1.0% by weight, adjusted to 100 μL, and mixed. After centrifugation at 5,000 rpm for 5 minutes, the supernatant was collected as much as possible, and collected in a 1.5-mL tube and stored at −20° C.

(2) Measurement of Release Rate

The release rate of the K(FAM)-G-P4 fusion peptide from the P4 peptide gel was measured according to the method in Example 6. The concentration of the K(FAM)-G-P4 fusion peptide released was determined based on an absorbance at 495 nm in the measurement of an UV absorption spectrum. The proportion (release rate (%)) of the amount of release at each time point of 0, 1, 4, 24, and 72 hours, relative to the initial amount of the K(FAM)-G-P4 fusion peptide which had been contained in the P4 peptide gel, was determined.

(Results)

Figure 14:
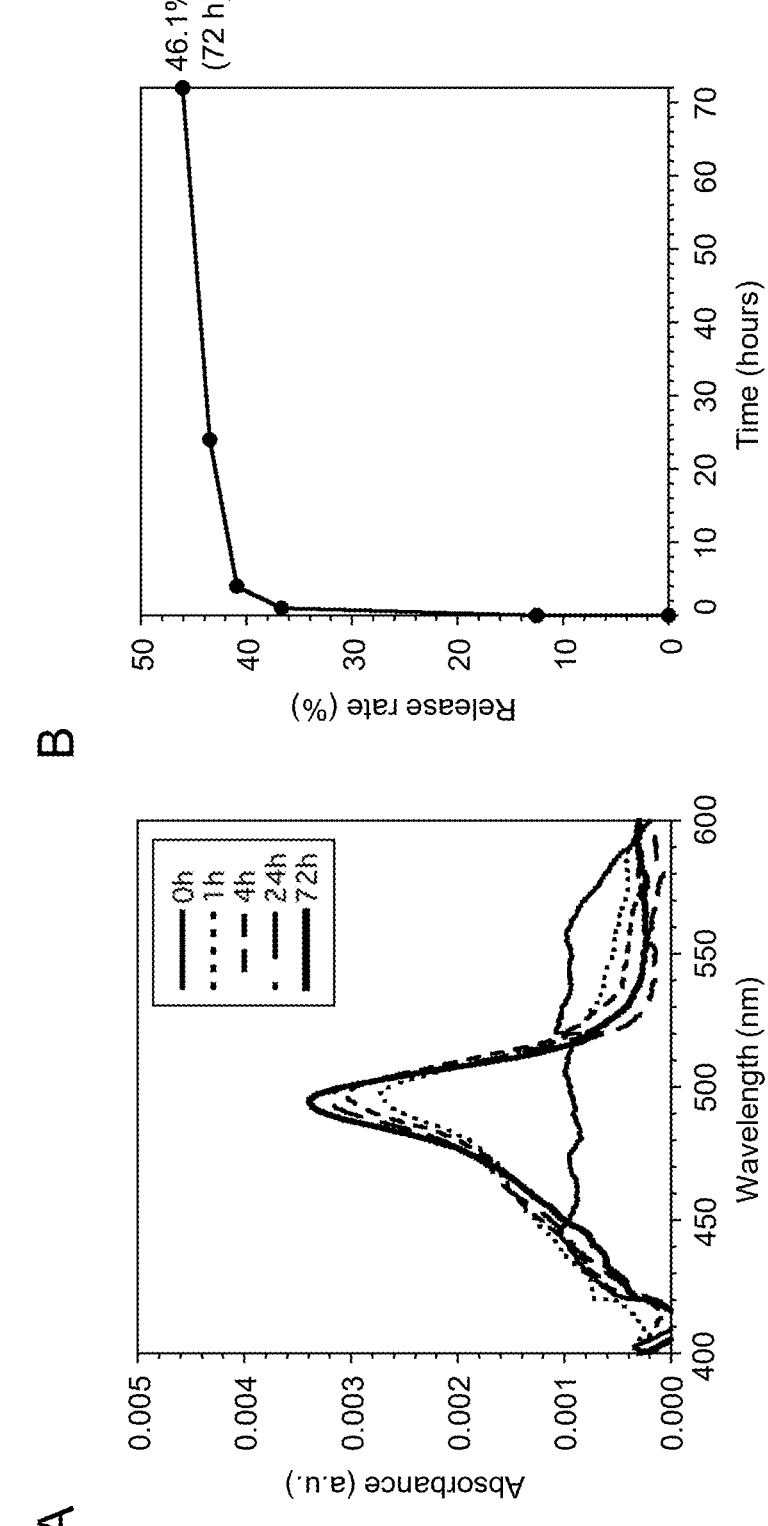
FIG. 14 shows the result of measuring the release rate of the K(FAM)-G-P4 fusion peptide from the P4 peptide gel.

FIG. 14 shows the results of measurement of the release rate of the K(FAM)-G-P4 fusion peptide from the P4 peptide gel. It was revealed that 46.1% of the K(FAM)-G-P4 fusion peptide was released over 72 hours. It was shown from the results that release from the P4 peptide gel was sustained over a long period of time even in the case of fusion of a small molecule to the P4 peptide.

Example 15: Production of Additional Self-Assembling Peptide and Fluidity Test (Purpose)

Additional self-assembling peptides which gel in physiological conditions are developed.

(Method and Results)

Additional five types of peptides: RIRGDMRADIR (SEQ ID NO: 41), RIRADMRGDIR (SEQ ID NO: 42), RIRGDIRGDIR (SEQ ID NO: 43), RIRGDIRADIR (SEQ ID NO: 44), and RIRADIRGDIR (SEQ ID NO: 45) were synthesized according to the same methods as in (1) to (3) of Example 1, and were subjected to gelling and fluidity test.

Figure 15:
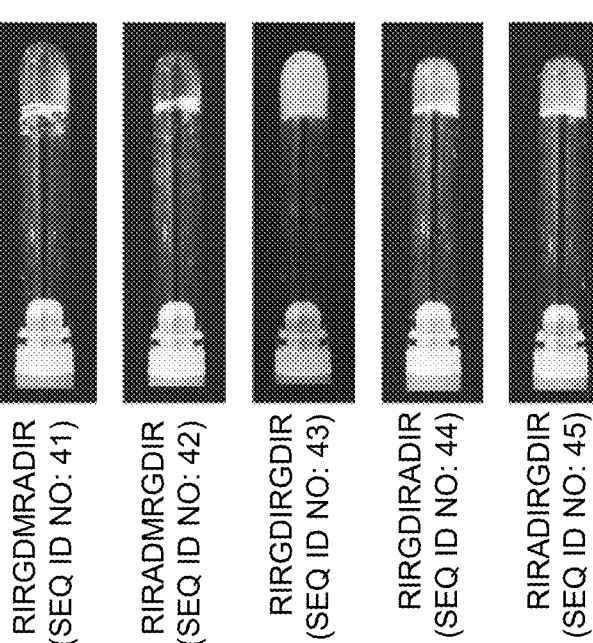
FIG. 15 shows the results of testing gel formation ability for additional five peptide samples. Gelling of the peptide sample was tested by the same method as in FIG. 1.

FIG. 15 shows the results of the fluidity test for each peptide sample. It was shown that RIRGDMRADIR (SEQ ID NO: 41), RIRADMRGDIR (SEQ ID NO: 42), RIRGDIRGDIR (SEQ ID NO: 43), RIRGDIRADIR (SEQ ID NO: 44), and RIRADIRGDIR (SEQ ID NO: 45) all remained on the bottom surface side of the microtube after vertical flipping of the microtube and were shown to have lost fluidity and gelled (FIG. 15).

All the publications, patents, and patent applications herein cited are herein incorporated by reference as they are.

The invention claimed is:

1. A hydrogelling self-assembling peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 41, SEQ ID NO: 42, SEQ ID NO: 43, SEQ ID NO: 44, and SEQ ID NO: 45.

2. A fusion peptide formed by linking a functional peptide to the self-assembling peptide of claim 1.

3. The fusion peptide of claim 2, wherein said linking is mediated by covalent bonding or supramolecular interaction.

4. The fusion peptide of claim 2, wherein the functional peptide is laminin, VEGF, or N-cadherin.

5. A gelling agent consisting of the self-assembling peptide of claim 1 or a fusion peptide formed by linking a functional peptide to said self-assembling peptide.

6. A gelling composition comprising the gelling agent of claim 5.

7. The gelling composition of claim 6, comprising two or more of the gelling agents.

8. A method of gelling, comprising
maintaining the gelling agent of claim 5 or a gelling composition comprising said gelling agent in a sol state, at a temperature not higher than the gelling temperature thereof in water or in an aqueous solution to thereby allow said gelling agent or said gelling composition to gel.

9. The method of claim 8, wherein said temperature at which said gelling agent or said gelling composition is maintained in water or in the aqueous solution is from 4 to 60° C.

10. The method of claim 8, wherein said gelling agent or said gelling composition comprises any one or more negative ions selected from the group consisting of a hydrogen carbonate ion, a carbonate ion, a citrate ion, a tartrate ion, and a sulfate ion.

11. The method of claim 8, wherein said gelling agent or said gelling composition in a gel state has a pH of from 6.0 to 8.0.

12. The method of claim 8, wherein the concentration of said gelling agent and/or said gelling composition is from 0.4% by weight to 10% by weight.

13. An artificial extracellular matrix comprising the self-assembling peptide of claim 1 or a fusion peptide formed by linking a functional peptide to said self-assembling peptide, wherein the self-assembling peptide or the fusion peptide is gelled.

14. A composition for preparing a sustained-release gel, comprising a gelling agent consisting of a first self-assembling peptide, and a functional molecule formed by linking a second self-assembling peptide and a functional moiety, wherein said first and second self-assembling peptides are selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 41, SEQ ID NO: 42, SEQ ID NO: 43, SEQ ID NO: 44, and SEQ ID NO: 45, wherein said functional moiety is a functional peptide and/or a low molecular weight compound.

15. The composition for preparing a sustained-release gel of claim 14, comprising two or more of the gelling agents.

16. The composition for preparing a sustained-release gel of claim 14, wherein said linking is mediated by covalent bonding or supramolecular interaction.

17. The composition for preparing a sustained-release gel of claim 14, wherein the functional peptide is selected from the group consisting of a vascular endothelial growth factor (VEGF), a fibroblast growth factor (FGF), and a hepatocyte growth factor (HGF).

18. A sustained-release gel comprising the composition for preparing a sustained-release gel of claim 14.

19. A pharmaceutical composition comprising the sustained-release gel of claim 18.

20. A method for producing a sustained-release gel, comprising:
mixing the composition for preparing a sustained-release gel of claim 14, with water or an aqueous solution; and
maintaining the mixture obtained after said mixing step, at a temperature not higher than the gelling temperature, to thereby allow the mixture to gel.

21. The method according to claim 20, wherein any one or more negative ions selected from the group consisting of a hydrogen carbonate ion, a carbonate ion, a citrate ion, a tartrate ion, and a sulfate ion are further mixed in said mixing step.

22. The method of claim 20, wherein said sustained-release gel in a gel state has a pH of 6.0 to 8.0.

23. The method according to claim 20, wherein the concentration of the gelling agent in said sustained-release gel is from 0.4% by weight to 10% by weight.

24. A fusion molecule formed by linking a self-assembling peptide and a functional moiety, wherein said self-assembling peptide is selected from the group consisting of SEQ ID NOs: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 41, SEQ ID NO: 42, SEQ ID NO: 43, SEQ ID NO: 44, and SEQ ID NO: 45, and wherein said functional moiety is a functional peptide and/or a low molecular weight compound.

* * * * *

SEQUENCE LISTING

```
<160> NUMBER OF SEQ ID NOS: 51

<210> SEQ ID NO 1
<211> LENGTH: 11
<212> TYPE: PRT
<213> ORGANISM: Artificial
<220> FEATURE:
<223> OTHER INFORMATION: synthetic

<400> SEQUENCE: 1

Arg Ile Arg Ala Arg Met Asp Ala Asp Ile Arg
1               5                   10

<210> SEQ ID NO 2
<211> LENGTH: 11
<212> TYPE: PRT
```

```
<213> ORGANISM: Artificial
<220> FEATURE:
<223> OTHER INFORMATION: synthetic

<400> SEQUENCE: 2

Arg Ile Arg Ala Asp Met Arg Ala Asp Ile Arg
1               5                   10

<210> SEQ ID NO 3
<211> LENGTH: 11
<212> TYPE: PRT
<213> ORGANISM: Artificial
<220> FEATURE:
<223> OTHER INFORMATION: synthetic

<400> SEQUENCE: 3

Arg Ile Arg Ala Asp Met Asp Ala Arg Ile Arg
1               5                   10

<210> SEQ ID NO 4
<211> LENGTH: 11
<212> TYPE: PRT
<213> ORGANISM: Artificial
<220> FEATURE:
<223> OTHER INFORMATION: synthetic

<400> SEQUENCE: 4

Arg Ile Asp Ala Arg Met Arg Ala Asp Ile Arg
1               5                   10

<210> SEQ ID NO 5
<211> LENGTH: 11
<212> TYPE: PRT
<213> ORGANISM: Artificial
<220> FEATURE:
<223> OTHER INFORMATION: synthetic

<400> SEQUENCE: 5

Arg Ile Asp Ala Arg Met Asp Ala Arg Ile Arg
1               5                   10

<210> SEQ ID NO 6
<211> LENGTH: 11
<212> TYPE: PRT
<213> ORGANISM: Artificial
<220> FEATURE:
<223> OTHER INFORMATION: synthetic

<400> SEQUENCE: 6

Arg Ile Asp Ala Asp Met Arg Ala Arg Ile Arg
1               5                   10

<210> SEQ ID NO 7
<211> LENGTH: 11
<212> TYPE: PRT
<213> ORGANISM: Artificial
<220> FEATURE:
<223> OTHER INFORMATION: synthetic

<400> SEQUENCE: 7

Arg Ile Arg Gly Asp Ile Arg Gly Asp Ile Arg
1               5                   10

<210> SEQ ID NO 8
<211> LENGTH: 11
<212> TYPE: PRT
<213> ORGANISM: Artificial
```

```
<220> FEATURE:
<223> OTHER INFORMATION: synthetic

<400> SEQUENCE: 8

Arg Ile Arg Gly Asp Met Arg Gly Asp Ile Arg
1               5                   10

<210> SEQ ID NO 9
<211> LENGTH: 11
<212> TYPE: PRT
<213> ORGANISM: Artificial
<220> FEATURE:
<223> OTHER INFORMATION: synthetic

<400> SEQUENCE: 9

Arg Ile Arg Ala Asp Ile Arg Ala Asp Met Arg
1               5                   10

<210> SEQ ID NO 10
<211> LENGTH: 11
<212> TYPE: PRT
<213> ORGANISM: Artificial
<220> FEATURE:
<223> OTHER INFORMATION: synthetic

<400> SEQUENCE: 10

Arg Ile Asp Ala Arg Met Arg Ala Asp Met Arg
1               5                   10

<210> SEQ ID NO 11
<211> LENGTH: 11
<212> TYPE: PRT
<213> ORGANISM: Artificial
<220> FEATURE:
<223> OTHER INFORMATION: synthetic

<400> SEQUENCE: 11

Arg Met Asp Ala Arg Ile Asp Ala Arg Ile Arg
1               5                   10

<210> SEQ ID NO 12
<211> LENGTH: 11
<212> TYPE: PRT
<213> ORGANISM: Artificial
<220> FEATURE:
<223> OTHER INFORMATION: synthetic

<400> SEQUENCE: 12

Arg Met Asp Ala Asp Met Arg Ala Arg Ile Arg
1               5                   10

<210> SEQ ID NO 13
<211> LENGTH: 11
<212> TYPE: PRT
<213> ORGANISM: Artificial
<220> FEATURE:
<223> OTHER INFORMATION: synthetic

<400> SEQUENCE: 13

Arg Val Arg Val Arg Val Asp Val Asp Val Arg
1               5                   10

<210> SEQ ID NO 14
<211> LENGTH: 11
<212> TYPE: PRT
<213> ORGANISM: Artificial
<220> FEATURE:
```

-continued

```
<223> OTHER INFORMATION: synthetic

<400> SEQUENCE: 14

Arg Val Arg Val Asp Val Arg Val Asp Val Arg
1               5                   10

<210> SEQ ID NO 15
<211> LENGTH: 11
<212> TYPE: PRT
<213> ORGANISM: Artificial
<220> FEATURE:
<223> OTHER INFORMATION: synthetic

<400> SEQUENCE: 15

Arg Val Arg Val Asp Val Asp Val Arg Val Arg
1               5                   10

<210> SEQ ID NO 16
<211> LENGTH: 11
<212> TYPE: PRT
<213> ORGANISM: Artificial
<220> FEATURE:
<223> OTHER INFORMATION: synthetic

<400> SEQUENCE: 16

Arg Val Asp Val Arg Val Arg Val Asp Val Arg
1               5                   10

<210> SEQ ID NO 17
<211> LENGTH: 11
<212> TYPE: PRT
<213> ORGANISM: Artificial
<220> FEATURE:
<223> OTHER INFORMATION: synthetic

<400> SEQUENCE: 17

Arg Val Asp Val Arg Val Asp Val Arg Val Arg
1               5                   10

<210> SEQ ID NO 18
<211> LENGTH: 11
<212> TYPE: PRT
<213> ORGANISM: Artificial
<220> FEATURE:
<223> OTHER INFORMATION: synthetic

<400> SEQUENCE: 18

Arg Val Asp Val Asp Val Arg Val Arg Val Arg
1               5                   10

<210> SEQ ID NO 19
<211> LENGTH: 16
<212> TYPE: PRT
<213> ORGANISM: Artificial
<220> FEATURE:
<223> OTHER INFORMATION: synthetic

<400> SEQUENCE: 19

Arg Ala Asp Ala Arg Ala Asp Ala Arg Ala Asp Ala Arg Ala Asp Ala
1               5                   10                  15

<210> SEQ ID NO 20
<211> LENGTH: 13
<212> TYPE: PRT
<213> ORGANISM: Artificial
<220> FEATURE:
<223> OTHER INFORMATION: synthetic
```

```
<400> SEQUENCE: 20

Arg Leu Asp Leu Arg Leu Ala Leu Arg Leu Asp Leu Arg
1               5                   10

<210> SEQ ID NO 21
<211> LENGTH: 155
<212> TYPE: PRT
<213> ORGANISM: Homo sapiens

<400> SEQUENCE: 21

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
        130                 135                 140

Ala Ile Leu Phe Leu Pro Met Ser Ala Lys Ser
145                 150                 155

<210> SEQ ID NO 22
<211> LENGTH: 728
<212> TYPE: PRT
<213> ORGANISM: Homo sapiens

<400> SEQUENCE: 22

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140
```

```
Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
                275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
                355                 360                 365

Asp Pro Asn Ile Arg Val Gly Tyr Cys Ser Gln Ile Pro Asn Cys Asp
        370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Asp Ala His
                435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
                515                 520                 525

Val Leu Thr Ala Arg Gln Cys Phe Pro Ser Arg Asp Leu Lys Asp Tyr
        530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
```

-continued

```
              565              570              575

Ser Asp Leu Val Leu Met Lys Leu Ala Arg Pro Ala Val Leu Asp Asp
         580              585              590

Phe Val Ser Thr Ile Asp Leu Pro Asn Tyr Gly Cys Thr Ile Pro Glu
       595              600              605

Lys Thr Ser Cys Ser Val Tyr Gly Trp Gly Tyr Thr Gly Leu Ile Asn
     610              615              620

Tyr Asp Gly Leu Leu Arg Val Ala His Leu Tyr Ile Met Gly Asn Glu
625              630              635              640

Lys Cys Ser Gln His His Arg Gly Lys Val Thr Leu Asn Glu Ser Glu
         645              650              655

Ile Cys Ala Gly Ala Glu Lys Ile Gly Ser Gly Pro Cys Glu Gly Asp
         660              665              670

Tyr Gly Gly Pro Leu Val Cys Glu Gln His Lys Met Arg Met Val Leu
       675              680              685

Gly Val Ile Val Pro Gly Arg Gly Cys Ala Ile Pro Asn Arg Pro Gly
     690              695              700

Ile Phe Val Arg Val Ala Tyr Tyr Ala Lys Trp Ile His Lys Ile Ile
705              710              715              720

Leu Thr Tyr Lys Val Pro Gln Ser
                725

<210> SEQ ID NO 23
<211> LENGTH: 23
<212> TYPE: DNA
<213> ORGANISM: Artificial
<220> FEATURE:
<223> OTHER INFORMATION: primer

<400> SEQUENCE: 23
ttgtcccaaa tctgtgcgga gcc                                           23

<210> SEQ ID NO 24
<211> LENGTH: 68
<212> TYPE: DNA
<213> ORGANISM: Artificial
<220> FEATURE:
<223> OTHER INFORMATION: primer

<400> SEQUENCE: 24
ttgagctctt accgtatatc tgctcgcatt cttgcgtcga tacgatgatg atgatgatga    60
tgtgcggc                                                            68

<210> SEQ ID NO 25
<211> LENGTH: 18
<212> TYPE: DNA
<213> ORGANISM: Artificial
<220> FEATURE:
<223> OTHER INFORMATION: primer

<400> SEQUENCE: 25
ggagccgaaa tctgggag                                                 18

<210> SEQ ID NO 26
<211> LENGTH: 31
<212> TYPE: DNA
<213> ORGANISM: Artificial
<220> FEATURE:
<223> OTHER INFORMATION: primer

<400> SEQUENCE: 26
```

```
tgctcgagtt accgtatatc tgctcgcatt c                                    31

<210> SEQ ID NO 27
<211> LENGTH: 165
<212> TYPE: PRT
<213> ORGANISM: Homo sapiens

<400> SEQUENCE: 27

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 28
<211> LENGTH: 9
<212> TYPE: PRT
<213> ORGANISM: Artificial
<220> FEATURE:
<223> OTHER INFORMATION: synthetic

<400> SEQUENCE: 28

Ile Arg Ala Arg Met Asp Ala Asp Ile
1               5

<210> SEQ ID NO 29
<211> LENGTH: 9
<212> TYPE: PRT
<213> ORGANISM: Artificial
<220> FEATURE:
<223> OTHER INFORMATION: synthetic

<400> SEQUENCE: 29

Ile Arg Ala Asp Met Arg Ala Asp Ile
1               5

<210> SEQ ID NO 30
<211> LENGTH: 9
<212> TYPE: PRT
<213> ORGANISM: Artificial
<220> FEATURE:
<223> OTHER INFORMATION: synthetic

<400> SEQUENCE: 30
```

```
Ile Arg Ala Asp Met Asp Ala Arg Ile
1               5

<210> SEQ ID NO 31
<211> LENGTH: 9
<212> TYPE: PRT
<213> ORGANISM: Artificial
<220> FEATURE:
<223> OTHER INFORMATION: synthetic

<400> SEQUENCE: 31

Ile Asp Ala Arg Met Arg Ala Asp Ile
1               5

<210> SEQ ID NO 32
<211> LENGTH: 9
<212> TYPE: PRT
<213> ORGANISM: Artificial
<220> FEATURE:
<223> OTHER INFORMATION: synthetic

<400> SEQUENCE: 32

Ile Asp Ala Arg Met Asp Ala Arg Ile
1               5

<210> SEQ ID NO 33
<211> LENGTH: 9
<212> TYPE: PRT
<213> ORGANISM: Artificial
<220> FEATURE:
<223> OTHER INFORMATION: synthetic

<400> SEQUENCE: 33

Ile Asp Ala Asp Met Arg Ala Arg Ile
1               5

<210> SEQ ID NO 34
<211> LENGTH: 9
<212> TYPE: PRT
<213> ORGANISM: Artificial
<220> FEATURE:
<223> OTHER INFORMATION: synthetic

<400> SEQUENCE: 34

Ile Arg Gly Asp Ile Arg Gly Asp Ile
1               5

<210> SEQ ID NO 35
<211> LENGTH: 9
<212> TYPE: PRT
<213> ORGANISM: Artificial
<220> FEATURE:
<223> OTHER INFORMATION: synthetic

<400> SEQUENCE: 35

Ile Arg Gly Asp Met Arg Gly Asp Ile
1               5

<210> SEQ ID NO 36
<211> LENGTH: 9
<212> TYPE: PRT
<213> ORGANISM: Artificial
<220> FEATURE:
<223> OTHER INFORMATION: synthetic

<400> SEQUENCE: 36
```

```
Ile Arg Ala Asp Ile Arg Ala Asp Met
1               5

<210> SEQ ID NO 37
<211> LENGTH: 9
<212> TYPE: PRT
<213> ORGANISM: Artificial
<220> FEATURE:
<223> OTHER INFORMATION: synthetic

<400> SEQUENCE: 37

Ile Asp Ala Arg Met Arg Ala Asp Met
1               5

<210> SEQ ID NO 38
<211> LENGTH: 9
<212> TYPE: PRT
<213> ORGANISM: Artificial
<220> FEATURE:
<223> OTHER INFORMATION: synthetic

<400> SEQUENCE: 38

Met Asp Ala Arg Ile Asp Ala Arg Ile
1               5

<210> SEQ ID NO 39
<211> LENGTH: 9
<212> TYPE: PRT
<213> ORGANISM: Artificial
<220> FEATURE:
<223> OTHER INFORMATION: synthetic

<400> SEQUENCE: 39

Met Asp Ala Asp Met Arg Ala Arg Ile
1               5

<210> SEQ ID NO 40
<211> LENGTH: 190
<212> TYPE: PRT
<213> ORGANISM: Mus Musculus

<400> SEQUENCE: 40

Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
            20                  25                  30

Glu Gln Lys Ser His Glu Val Ile Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Ala Gly Cys Cys Asn Asp Glu Ala Leu Glu Cys Val Pro Thr
                85                  90                  95

Ser Glu Ser Asn Ile Thr Met Gln Ile Met Arg Ile Lys Pro His Gln
            100                 105                 110

Ser Gln His Ile Gly Glu Met Ser Phe Leu Gln His Ser Arg Cys Glu
        115                 120                 125

Cys Arg Pro Lys Lys Asp Arg Thr Lys Pro Glu Asn His Cys Glu Pro
    130                 135                 140

Cys Ser Glu Arg Arg Lys His Leu Phe Val Gln Asp Pro Gln Thr Cys
145                 150                 155                 160
```

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190

<210> SEQ ID NO 41
<211> LENGTH: 11
<212> TYPE: PRT
<213> ORGANISM: Artificial
<220> FEATURE:
<223> OTHER INFORMATION: synthetic

<400> SEQUENCE: 41

Arg Ile Arg Gly Asp Met Arg Ala Asp Ile Arg
1               5                   10

<210> SEQ ID NO 42
<211> LENGTH: 11
<212> TYPE: PRT
<213> ORGANISM: Artificial
<220> FEATURE:
<223> OTHER INFORMATION: synthetic

<400> SEQUENCE: 42

Arg Ile Arg Ala Asp Met Arg Gly Asp Ile Arg
1               5                   10

<210> SEQ ID NO 43
<211> LENGTH: 11
<212> TYPE: PRT
<213> ORGANISM: Artificial
<220> FEATURE:
<223> OTHER INFORMATION: synthetic

<400> SEQUENCE: 43

Arg Ile Arg Gly Asp Ile Arg Gly Asp Ile Arg
1               5                   10

<210> SEQ ID NO 44
<211> LENGTH: 11
<212> TYPE: PRT
<213> ORGANISM: Artificial
<220> FEATURE:
<223> OTHER INFORMATION: synthetic

<400> SEQUENCE: 44

Arg Ile Arg Gly Asp Ile Arg Ala Asp Ile Arg
1               5                   10

<210> SEQ ID NO 45
<211> LENGTH: 11
<212> TYPE: PRT
<213> ORGANISM: Artificial
<220> FEATURE:
<223> OTHER INFORMATION: synthetic

<400> SEQUENCE: 45

Arg Ile Arg Ala Asp Ile Arg Gly Asp Ile Arg
1               5                   10

<210> SEQ ID NO 46
<211> LENGTH: 9
<212> TYPE: PRT
<213> ORGANISM: Artificial
<220> FEATURE:
<223> OTHER INFORMATION: synthetic

```
<400> SEQUENCE: 46

Ile Arg Gly Asp Met Arg Ala Asp Ile
1               5

<210> SEQ ID NO 47
<211> LENGTH: 9
<212> TYPE: PRT
<213> ORGANISM: Artificial
<220> FEATURE:
<223> OTHER INFORMATION: synthetic

<400> SEQUENCE: 47

Ile Arg Ala Asp Met Arg Gly Asp Ile
1               5

<210> SEQ ID NO 48
<211> LENGTH: 9
<212> TYPE: PRT
<213> ORGANISM: Artificial
<220> FEATURE:
<223> OTHER INFORMATION: synthetic

<400> SEQUENCE: 48

Ile Arg Gly Asp Ile Arg Gly Asp Ile
1               5

<210> SEQ ID NO 49
<211> LENGTH: 9
<212> TYPE: PRT
<213> ORGANISM: Artificial
<220> FEATURE:
<223> OTHER INFORMATION: synthetic

<400> SEQUENCE: 49

Ile Arg Gly Asp Ile Arg Ala Asp Ile
1               5

<210> SEQ ID NO 50
<211> LENGTH: 9
<212> TYPE: PRT
<213> ORGANISM: Artificial
<220> FEATURE:
<223> OTHER INFORMATION: synthetic

<400> SEQUENCE: 50

Ile Arg Ala Asp Ile Arg Gly Asp Ile
1               5

<210> SEQ ID NO 51
<211> LENGTH: 16
<212> TYPE: PRT
<213> ORGANISM: Artificial
<220> FEATURE:
<223> OTHER INFORMATION: synthetic

<400> SEQUENCE: 51

Lys Lys Gln Phe Gln Leu Gln Phe Gln Leu Gln Phe Gln Leu Lys Lys
1               5                   10                  15
```